US012685987B2

(12) United States Patent
Aemissegger et al.

(10) Patent No.: US 12,685,987 B2
(45) Date of Patent: Jul. 21, 2026

(54) APPARATUS FOR THE SYNTHESIS OF OLIGONUCLEOTIDES AND PROCESS FOR THE PREPARATION THEREOF

(71) Applicant: BACHEM AG, Bubendorf (CH)

(72) Inventors: Andreas Aemissegger, Pratteln (CH); Branislav Dugovic, Bern (CH); Mario Jauker, Loerrach (DE); Martin Stauss, Rheinfelden (DE)

(73) Assignee: BACHEM AG, Bubendorf (CH)

( * ) Notice: Subject to any disclaimer, the term of this patent is extended or adjusted under 35 U.S.C. 154(b) by 1085 days.

(21) Appl. No.: 17/779,688

(22) PCT Filed: Dec. 2, 2020

(86) PCT No.: PCT/EP2020/084324
§ 371 (c)(1),
(2) Date: May 25, 2022

(87) PCT Pub. No.: WO2021/110773
PCT Pub. Date: Jun. 10, 2021

(65) Prior Publication Data
US 2022/0401910 A1 Dec. 22, 2022

(30) Foreign Application Priority Data

Dec. 2, 2019 (EP) .................................... 19212971

(51) Int. Cl.
B01J 19/00 (2006.01)
B01F 25/40 (2022.01)
(Continued)

(52) U.S. Cl.
CPC ........... B01J 19/0046 (2013.01); B01F 25/40 (2022.01); B01J 4/008 (2013.01); B01J 19/0013 (2013.01);
(Continued)

(58) Field of Classification Search
CPC .... B01J 19/0046; B01J 4/008; B01J 19/0013; B01J 19/0066; B01J 2219/0068;
(Continued)

(56) References Cited

U.S. PATENT DOCUMENTS

| 4,598,049 A | * | 7/1986 | Zelinka | .................. | C07H 21/00 |
| | | | | | 422/111 |
| 5,681,534 A | | 10/1997 | Neves | | |
| 2008/0058512 A1 | * | 3/2008 | Leproust | ................ | C07H 21/00 |
| | | | | | 536/25.3 |

FOREIGN PATENT DOCUMENTS

| EP | 0984021 | A2 | 3/2000 |
| JP | S6458340 | A | 3/1989 |
| JP | 2014-47169 | A | 3/2014 |
| WO | 9706884 | A1 | 2/1997 |
| WO | 9943694 | A1 | 9/1999 |

OTHER PUBLICATIONS

Machine translation of JP_2014047169 A (Year: 2025).*
(Continued)

*Primary Examiner* — Huy Tram Nguyen
(74) *Attorney, Agent, or Firm* — RAPHAEL BELLUM PLLC

(57) ABSTRACT
The present invention provides apparatuses and methods for the synthesis of oligonucleotides and related compounds. In particular, the present invention allows to effectively prepare reagents to be fed into an apparatus for the synthesis of such oligomers.

22 Claims, 13 Drawing Sheets

(51) Int. Cl.
    *B01J 4/00*           (2006.01)
    *C07H 1/02*        (2006.01)
(52) U.S. Cl.
    CPC ............ *B01J 19/0066* (2013.01); *C07H 1/02*
        (2013.01); *B01J 2219/0068* (2013.01); *B01J*
        *2219/00698* (2013.01)
(58) Field of Classification Search
    CPC .... B01J 2219/00698; B01J 2219/00351; B01J
        2219/00722; B01F 25/40; C07H 1/02;
        C07H 21/00; Y02P 20/55
    USPC ........................................................ 422/129
    See application file for complete search history.

(56)          References Cited

OTHER PUBLICATIONS

Xu Xindonget et al. "Research Progress in De Novo Synthesis and Design of Biological Macromolecules" Advances in Biochemistry and Biophysics, 46:8 p. 772-786, 2019.
English-language translation of excerpt of summary of Chinese Office Action dated Jan. 17, 2024 for CN 202080095306.3.
International Preliminary Report on Patentability in International Application No. PCT/EP2020/084324, dated May 17, 2022.
Reese, "Oligo- and poly-nucleotides: 50 years of chemical synthesis," Org. Biomol. Chem 3: 3851-3868 (2005).
Septak, "Kinetic studies on depurination and detritylation of tPG-baund Intenmedlates duning oligonucleotide synthesis," Nucleic Acids Research 24(15): 3053-3058 (1996).

* cited by examiner

APPARATUS FOR THE SYNTHESIS OF OLIGONUCLEOTIDES AND PROCESS FOR THE PREPARATION THEREOF

The present invention generally relates to the field of oligomer synthesis at an industrial or laboratory scale. Improved methods and apparatuses for the synthesis of oligomers, in particular of oligonucleotides and related polymers, are disclosed. In particular, the present invention allows to effectively prepare reagents to be fed into an apparatus for the synthesis of such oligomers.

Oligonucleotides and related oligomers may be produced by various synthesis strategies including the commonly used phosphoramidite method. The synthetic strategies commonly comprise the stepwise addition of monomeric or oligomeric building blocks, e.g. of nucleoside phosphoramidites, to a growing oligomer chain. Usually, the growing oligomer chain is made up of nucleotides or their analogs and is immobilized to a solid support, e.g. via a hydroxyl group of the ribose moiety. Reactive groups on the oligomer chain are blocked from unintended reaction by suitable protecting groups. For example, the growing oligonucleotide chain may be immobilized via the 3' hydroxyl group to a solid support and may carry protective groups such as those listed in table 1 to block hydroxyl moieties of the ribose moiety and exocyclic amino groups of the base moieties from reactions.

TABLE 1

Non-limiting selection of common protecting groups used in oligonucleotide synthesis

| Protecting group | Often used for |
|---|---|
| DMT = 4,4-dimethoxytrityl | acid-labile protection of 5' OH-group |
| Bz = benzoyl;<br>iBu = isobutyryl;<br>PAC = phenoxyacetyl | exocyclic amino group of adenine |
| Ac = acetyl | exocyclic amino group of cytosine |
| iBu = isobutyryl;<br>i-Pr-PAC = 4-isopropylphenoxyacetyl);<br>DMF = dimethylformamidino | exocyclic amino group of guanine |
| TBDMS = t-butyldimethylsilyl;<br>TOM = tri-iso-propylsilyloxymethyl | protection of 2' OH-group |

Generally speaking, iterative methods of chemical oligonucleotide synthesis usually rely on the use of a first type of protecting groups for those functional groups located in the base/base analog and ribose/ribose analog moieties, which are not involved in chain elongation, and on the use of a second type of temporary protecting group for controlling backbone extension: The temporary protecting group is located on the building block to be added in order to avoid double insertions of the building block or multimerization of building block moieties. The first and second type of protecting groups are orthogonal to each other, meaning that one type can be removed under conditions, which do not affect the other type of protecting group. Commonly, the first type of protecting groups are cleavable under alkaline conditions and are "permanent" in that they will only be removed once chain assembly is complete; the second type of temporary protecting group is cleavable under acidic conditions and is removed once per synthetic cycle. The coupling cycles therefore comprise a step of coupling a protected building block to an unprotected end of the oligonucleotide backbone, followed by deprotection of the thus-extended oligonucleotide in order to prepare for the subsequent coupling cycle.

For phosphoramidite oligonucleotide synthesis, the synthesis cycle usually starts by selective deprotection of the 5' hydroxyl group, which is achieved by incubation of the solid support with a deprotecting reagent DR, commonly a detritylation reagent allowing to remove the DMT group. Next, the growing oligonucleotide chain is incubated with a coupling reagent CR comprising an appropriately protected nucleoside phosphoramidite and activating reagents. The tricoordinated phosphite triester resulting from the coupling reaction is then oxidized using an oxidizing reagent OR to yield a phosphate triester. In the case of phosphorothioate or phosphorodithioate synthesis, sulfurization instead of oxidation will be carried out using a sulfurization reagent SR and will yield a phosphorothioate triester. A capping step involves incubating the solid support with a capping reagent, also referred to as blocking reagent BR to block any unreacted groups on the resin, thereby avoiding the occurrence of deletion sequences in subsequent coupling rounds. In other cases, capping may be carried out before or after oxidation of the tricoordinated phosphite triesters. Between each of the steps, the resin may be washed with a process solvent, typically acetonitrile or toluene. The growing oligonucleotide chain may be immobilized to the solid support in any conceivable way, e.g. via the exocyclic amine or via the ribose/ribose analog moieties' hydroxyl groups. In addition, variations of phorphoramidite synthesis have been disclosed, such as a reverse 5'-3' oligonucleotide synthesis, where 5'-phosphoramidites are added.

For phosphonate oligonucleotide synthesis, nucleoside H-phosphonate monoesters with an acid sensitive temporary protecting group such as DMT are used. The internucleosidic H-phosphonate diester linkages are oxidized at the end of the chain assembly. Depending on the reaction conditions used, phosphodiester linkages, phosphorthioate linkages, phosphorselenoates or phosphoramidate analogs may be generated in this step.

The above-mentioned reagents may vary in their composition depending on the exact protocol used. Table 2 gives a non-limiting summary of commonly used compositions.

TABLE 2

Non-limiting examples of reagent mixtures used for oligonucleotide synthesis

| Reagent mixture | Exemplary composition |
|---|---|
| deprotecting reagent DR | Tricholoroacetic acid* (TCA) in dichloromethane (DCM)<br>Tricholoroacetic acid* (TCA) in toluene<br>Dichloroacetic acid* (DCA) in dichloromethane (DCM)<br>Dichloroacetic acid* (DCA) in toluene |
| coupling reagent CR | nucleoside phosphoramidite, acidic azole catalyst in anhydrous acetonitrile (ACN) |
| oxidizing reagent OR | Iodine*, weak base in water<br><br>tBu Hydroperoxide in toluene<br>(1S)-(+)-(10-camphorsulfonyl)-oxaziridine in acetonitrile |
| sulfurization reagent SR | Phenylacetyl disulfide and weak base (e.g. pyridine, 3-picoline, lutidine, collidine) in acetonitrile<br>Xanthane hydride and weak base in acetonitrile<br>Phenyl-3H-1,2,4-dithiazol-3-one in acetonitrile |
| blocking reagent BR | Acetic anhydride*, weak base, N-methylimidazole in acetonitrile |

*corrosive reagent

Documents US 2008/0058512 and U.S. Pat. No. 5,681, 534 disclose apparatuses for oligonucleotide preparation. Commercially available automated oligonucleotide synthesizers are constructed such that the deprotection solution DS, the oxidizing solution OS, and the sulfurization solution SS are provided pre-made in tanks and are applied to the synthesis reactor by means of one or more pumping circuits. The blocking solution BS is prepared by inline mixing of two premade solutions. The coupling solutions CS is mixed in the synthesizer by combining a solution of the phosphoramidite in acetonitrile with a solution of the activator This layout is however disadvantageous in that it does not allow "fine-tuning" the reagent composition for specific coupling cycles, e.g. by varying the concentration of the deprotecting agent. Moreover, it requires to provide an extensive collection of tanks, with the tank volume limiting the scale-up of synthesis. In order to overcome these problems, the present invention provides an improved apparatus for oligonucleotide synthesis, where all reagents may be prepared on demand by in-line mixing. Pure liquid reagents may be fed into the system straight from their respective storage containers. Those reagents, which are not liquids, may be fed into the system as concentrated stock solutions. As a further improvement, the present invention provides an apparatus for oligonucleotide synthesis comprising a batch reactor instead of a column bed reactor, thereby offering further options to carry out and control the synthesis process.

In one particular aspect, the present invention provides a method for "fine tuning" the composition of the deprotecting reagent by defining the composition of this reagent for each coupling cycle. It has been reported before that the deprotection step needs to walk a fine line between avoiding acid-catalyzed degradation of the oligonucleotide intermediates, e.g. due to depurination, and achieving efficient removal of the protecting group. To solve this issue, various deprotection compositions have been compared, and, e.g. Septak teaches to use 15% DCA rather than 3% DCA or 3% TCA (Nucleic Acids Research, 1996, Vol. 24, No. 15 3053-3058). However, to the knowledge of the present inventors, all automated methods of oligonucleotide synthesis rely on the use of the same deprotection agent in all cycles of a given synthesis. By contrast the present invention provides an apparatus and method for adjusting the composition of the deprotecting reagent individually for each coupling cycle.

One embodiment of the present invention therefore relates to an apparatus for the automated synthesis of oligonucleotides, comprising:

a) a reaction vessel connected via a liquid conduit to a waste container;

b) a liquid supply unit for delivering liquid reagents to the reaction vessel;

c) a bypass conduit, which allows to direct liquid flow from the liquid supply unit into the waste container without passage through the reaction vessel; and d) a control unit characterized in that the liquid supply unit comprises:

b-1) at least one mixing device, connected to b-2) at least two liquid supply lines, each comprising at least one liquid conduit with n liquid inlets, where n is an integer between 1 and 25, and at least one liquid pump.

Another aspect of the present invention therefore relates to an apparatus for synthesis of oligomers, comprising:

a) a reaction vessel connected via a liquid conduit to a waste container;

b) a liquid supply unit for delivering liquid reagents to the reaction vessel;

c) a bypass conduit, which allows to direct liquid flow from the liquid supply unit into the waste container without passage through the reaction vessel; and d) a control unit wherein the liquid supply unit comprises:

b-1) at least one mixing device, connected to b-2) at least 4 upstream liquid supply lines, each comprising one liquid conduit with n liquid inlets, where n is an integer between 1 and 25, and one liquid pump; and b-3) n sensors, where n is an integer equal to or bigger than 1, which sensor(s) is/are positioned downstream of the mixing device and determine(s) at least one property of the liquid emerging from the mixing device, wherein at least one readout provided by the sensor(s) is used as a feedback signal to regulate the activity of one or more of said liquid pumps.

Preferably, the apparatus is used for the solid-phase synthesis of oligonucleotides, in particular of ribonucleic acids, 2'-deoxyribonucleic acids, oligonucleotide phosphorothioates, xenonucleic acids and related molecules. In some embodiments, the apparatus is used for methods of solid phase synthesis by the phosphoramidite method.

As used herein, the expression "oligonucleotide" is used in a most general way to relate to any oligomers comprising at least two nucleoside units linked by a phosphodiester moiety or by an analogous structure, as is present, e.g., in phosphorothioates, phosphorodithioates, diastereomerically pure phosphorothioates, phosphoramidates. phosphorodiamidates, arsenate diesters and phosphoroselenoates Naturally occurring nucleoside units typically comprise a ribose or a 2'-desoxy ribose moiety, and a nucleobase selected from adenine, guanine, cytosine, thymine, and uracil. As used herein, the expression nucleoside unit encompasses the naturally occurring nucleosides as well as artificial compounds. The latter may carry substituents in the ribose/ribose analog moiety, e.g. —F, —OMe (—O—CH3), or -methoxyethyl (—O—CH2-CH2-O—CH3, aka. MOE, —O—methoxyethyl) substituents, or the ribose may be modified with an extra methylene bridge connecting the 2' hydroxyl group with the 4' carbon, or the ribose moiety may be replaced by another cyclic monosaccharide, such as a pentose (e.g. arabinose) or a hexose, by a non-cyclic monosaccaride (e.g. threose), or by an alternative structure such as, e.g., cyclohexen, threoninol, serinol, or glycol. All of these entities may be referred to as "ribose analog" herein. Likewise, artificial nucleosides may exhibit non-standard bases, artificial analogs of nucleobases or abasic sites. Non-limiting examples of oligonucleotides beyond desoxyribonucleic acids (DNA) and ribonucleic acids (RNA) are locked nucleic acids (LNA), amino LNA, constrained ethyl nucleic acid analogs (cET), bridged nucleic acids (BNA), tricycloDNA, unlocked nucleic acids (UNA), phosphoramidite morpholino oligonucleotides (PMO) iRNA, dsRNA, and oligonucleotide phosphorothioates, as well as derivatives and analogs thereof.

As used herein, the expression "liquid supply unit" is used to refer to those parts of the apparatus according to the present invention, which function to provide the liquid reagents to be charged into the reactor (reaction vessel). In particular, a liquid supply unit may comprise one or more liquid inlets, storage vessels or liquid tanks, liquid conduits, pumps, valves, liquid mixing devices, heat exchangers, manifolds, and sensors.

As used herein, the expression "liquid supply line" is used to refer to a liquid conduit comprising a liquid pump and one or more liquid inlet(s), which may be connected to one or more liquid containers. The fluid connection between each of the liquid inlets and the conduit may be regulated by means of a valve. The liquid supply line may thus provide a controlled liquid flow from one or more of said liquid inlets/containers to a downstream device. The pump and valves may be controlled by a local control unit and/or by a central control unit. In some embodiments, each liquid supply line has between 1 and 25, preferably between 3 and 10 inlets. One or more of such inlets may be connected to a branched liquid conduit, which in turn is connected to a multitude of storage vessels. The outermost inlets of each of the liquid supply lines may be connected to supplies of process solvent and of liquid nitrogen in order to enable purging of the line between process steps.

In some embodiments, the liquid supply unit of the apparatus further comprises a third liquid supply line connected to the mixing device, said third liquid supply line comprising at least one liquid conduit with n liquid inlets, where n is an integer between 1 and 25, and at least one liquid pump.

As used throughout this document, two parts of the present apparatus may be said to be "connected" if they are receiving input from one another. For example, the parts may be joined by a liquid conduit allowing the passage of liquid from one part to another.

The liquid inlets may be connected to storage vessels, which may be adapted to keep their contents under inert gas. For example, the vessel may comprise a controllable valve, which can be connected to a vacuum source, and with a second controllable valve, which can be connected to a source of inert gas such as nitrogen. For automated inertization, the storage vessel may additionally comprise an electronic or mechanical pressure controller and the valves may be operated automatically. For manual inertization, the storage vessel may comprise a pressure indicator and manually controlled valves.

The storage vessel(s) may be made of any suitable material, e.g. of metals, enamel, or polymers such as polypropylene, polyethylene, polyvinyl chloride, polystyrene, and polyether ether ketone. Preferably, a material is chosen, which is essentially inert against the reagents it will be exposed to. Depending on their content, different storage vessels may be made from the different materials.

Preferably, the material is compliant with the applicable regulations for the production of pharmaceutical products, cosmetics and/or food and beverages, i.e. it complies with good manufacturing practices (GMP). Further, to minimize the risk of electrostatic ignition, an electrically conductive material may be used. In some embodiments, the storage vessel is made of stainless steel or Hastelloy® alloys or of a metal coated with an electrically conductive polymer. The size of the storage vessels can be chosen according to the scale of synthesis intended, and storage vessels of different sizes may be used at the same time, depending on their content. In some embodiments, the storage vessels may have an inner volume of about 1 liter (L) to 40 cubic meters e.g. about 1, 5, 10, 15, 20, 25, 30, 35, 40, 45, 50, 100, 150, 200, 550, 770, 990, 1120, 1300, 1500 L. In some embodiments, some of the storage vessels may have an inner volume of about 10 to 40 liters. In some embodiments, the storage vessels for the process solvents, e.g. for acetonitrile and toluene, may be tanks with a volume of 20 to 40 cubic meters. Other reagents, such as the solutions of specific protected nucleoside phosphoramidites, may be provided in much smaller storage vessels with a volume of about 1 or 5 liters.

The skilled person will understand that any reaction vessel may be used with the liquid supply unit described above. The reaction vessel may be made of any suitable material e.g. of metals, glass, enamel, or polymers such as polypropylene, polyethylene, polyvinyl chloride, polystyrene, and poly ether ether ketone. Preferably, a material is chosen, which is essentially inert against the reagents it will be exposed to and which is compliant with good manufacturing practices (GMP). Further, to minimize the risk of electrostatic ignition, an electrically conductive material may be used. The size and dimensions of the reaction vessel can be chosen according to the scale of synthesis intended. For example, column reactors with a maximal inner volume of 5, 10, 30, 40, 50, 60, 70, 75, 80, 90, 100, 150, or 200 liters may be used. As further examples, batch reactors with a maximal inner volume of 5, 10, 30, 40, 50, 60, 70, 75, 80, 90, 100, 150, 200, 250, 300, 450, 600 or 650 liters may be used. As further examples, reactors with an inner volume of 100 or 200 ml may be used. In some embodiments of the invention, the inner volume of the reaction vessel is about 30-250 liters, preferably about 40 to 200 liters, most preferably about 40 to 150 liters. As used herein, the expression "about" indicates that deviations by plus or minus 10% of the value given are possible.

For example, solid phase oligonucleotide synthesis is commonly carried out using column reactors packed with a solid support, to which the growing oligonucleotide chain is tethered. The column reactors may typically comprise a bottom frit and a top frit, with the solid support packed between. Solid supports are available from a variety of vendors with or without a first protected nucleotide of choice attached to the support.

In particular if using a column reactor, it may be advantageous to circulate the reagent mixtures over the column by means of a pump. Therefore, in some embodiments, the present apparatus further comprises a recycling circuit directing flow from the liquid conduit, which connects the reaction vessel to the waste container, back into the reaction vessel by means of a pump. The recycling circuit may be integrated into one of the liquid supply lines of the apparatus. In this case, the recycling circuit is comprised in one of the liquid supply lines, which is connected via one of its inlets and a multi way valve to the liquid conduit, and whose pump may drive the recirculation of the fluid from the liquid conduit, which connects the reaction vessel and the waste container, via the mixing device back into the reaction vessel. The recirculation circuit may be arranged such that the direction of the liquid flow through the column may be reversed. For example, a column reactor may be connected to the liquid supply unit via a valve assembly allowing liquid to flow through the reactor in the forward and reverse direction, as well as bypass the reactor completely.

As an alternative, the inventors found that a batch reactor may be used. This reactor may comprise a bottom frit or filter cloth to retain the support inside the reactor, a mixing device, and one or more spray balls or nozzles for rinsing the inner surfaces of the reactor. A rotating or a fixed spray ball or nozzle may be used, which is/are positioned in the top part of the reaction vessel and is/are connected to a liquid source. The skilled person will routinely choose the mixing device in dependence of the materials to be mixed, e.g. with respect of the physical robustness of the support used. For example, a stirrer comprising a rotating impeller may be used. Such an impeller may be a turbulent mixer causing axial, mixed, or radial flow of the liquid inside the reaction vessel. Known impellers include marine-type propellers, pitch-blade turbines, flat-blade turbines, and flat-blade paddles. The use of baffle blades may be helpful to improve mixing. Alternatively or in addition, mixing may be achieved by bubbling gas through the liquid. Alternatively or in addition, mixing may be achieved by liquid circulation, e.g. by means of a pumping circuit. A person skilled in the art will usually choose the mixing means so as to achieve efficient distribution of substances inside the reaction medium while avoiding foaming. When using solid supports inside the reaction vessel, the vessel and stirrer blades are preferably designed so as to minimize shearing forces. Preferably, the actions of the mixing device may be controlled by the control unit. The batch reactor may preferably be adapted for working under protective atmosphere. For example, the reaction vessel of the batch reactor may comprise a first controllable valve, which can be connected to a vacuum source, a second controllable valve, which can be connected to a source of inert gas such as nitrogen, and an electronic or mechanical pressure controller. Preferably, the valves may be operated automatically and are under the control of the control unit. To facilitate temperature control, the batch reactor may be a jacketed reactor. The use of a batch reactor has several advantages over a packed column reactor in that it allows for sampling of the solid material and in that the reaction conditions may be more homogenous throughout the reactor.

Therefore, another embodiment of the present invention relates to an apparatus for the solid phase synthesis of oligonucleotides, characterized in that the synthesis is carried out inside a batch reactor. In some embodiments, said reactor comprises a mixing device, one or more spray balls or nozzles for rinsing the inner surfaces of the reactor, and is adapted for working under protective gas.

The skilled person is well aware of the fact that various valves, preferably automated valves, may be used to control the liquid flow throughout the apparatus. For example, liquid flow into the reaction vessel and out of the reaction vessel may be controlled by means of valves integrated into ingoing and outgoing liquid conduits.

The skilled person will understand that any mixing device may be used with the present invention, which allows to combine a minimum of 2 liquid influxes, e.g. 3 or 4 influxes, into one homogenous solution. The skilled person will therefore choose the mixing device such that is fits in the context of the specific apparatus in terms of mixing effect, size, and pressure drop. The mixing device may consist of or comprise a series of mixing tees or mixing crosses, which successively unite the at least two incoming flows. The mixing device may comprise one or more mixing tees or T valves and a heat exchanger. The mixing device may comprise a static mixer. The mixing device may consist of or comprise a static mixer with at least 2 inlets and one outlet. In some embodiments, the mixing device may consist of or comprise a multi way valve, e.g. a T-valve, and a static mixer. The multi way valve and the static mixer may be arranged such that several flows are united by the valve and then guided through the static mixer. The mixing device may consist of or comprise a manifold combining the liquid flows of at least two liquid supply lines and directing the combined flow into a static mixer or into a heat exchanger. The mixing device may be jacketed to allow for heating or cooling of the mixed liquid.

In one embodiment, at least the inner surfaces of the mixing device and of one of the liquid supply lines are made from an acid-resistant material. This means that at least the inner surfaces of one liquid supply line from at least one of the liquid inlets, via the pump, up to and including the mixing device are made of or coated with an acid resistant material. As used herein, "acid-resistant" may mean that a material is found resistant or essentially inert towards acidic solutions, e.g. towards a solution of 50% DCA (dichloroacetic acid) in toluene with 200 ppm water. Acid resistance may also be assessed using solutions of 100% DCA comprising 200 ppm water. Materials may be tested for this property using well established procedures such as laid out in DIN 50905-4 from March 2018. A metal material may be classified as acid resistant, if it shows no signs of local corrosion and if the loss of material is below 0.01 mm/year upon exposure to acid containing liquid. A metal material may be classified as acid resistant, if it does not release significant amounts of leachables or extractables into an acid solution it is exposed to. Such amounts may be considered significant, if they yield detectable contaminations of the oligomer to be synthesized, which are not acceptable for a pharmaceutical ingredient according to established guidelines by the regulatory authorities. The material may be considered acid resistant, e.g. resistant to a solution of 50% DCA (dichloroacetic acid) in toluene with 200 ppm water or to 100% DCA, if it does not release amounts of leachables or extractables, which may be detected in the oligonucleotide synthesized. In one embodiment, at least the inner surfaces of the mixing device and of one of the liquid supply lines are made from an acid-resistant alloy. Further, at least the inner surfaces of the mixing device and of one of the liquid supply lines may comprise an acid-resistant polymeric coating or a glass coating. For example, the acid-resistant material may be selected from the group consisting of highly resistant nickel-base alloys, polymeric coatings, and glass linings. Suitable polymeric coatings comprise polytetrafluoroethylene (PTFE), perfluoroalkoxy alkanes (PFA), ethylene tetrafluoroethylene (ETFE), or ethylene chlorotrifluoroethylene (ECTFE). Suitable nickel-base alloys comprise, e.g., Hastelloy® C-4, C22, C-2000, and C276 alloys, which are identified by the material number/Unified Numbering System for Metals and Alloys(UNS) numbers: 2.4610/N06455, 2.4602/NO06022, 2.4675/NO6200 and 2.4819/N10276, respectively.

The apparatus according to the present invention may further comprise n sensors, where n is an integer equal to or larger than 1, which sensor(s) is/are positioned downstream of the mixing device and determine(s) at least one property of the liquid emerging from the mixing device.

The n sensor(s) may serve to analyze the composition of the liquid emerging from the mixing device, thereby providing a signal to a control unit. For example, at least one readout provided by at least one of the sensor(s) may be used as a feedback signal to regulate the activity of one or more of the pumps comprised in the liquid supply unit. This may allow to regulate the flows from the liquid pumps into the mixing device so as to achieve and maintain a given set value. Hence, the sensors may be part of a feedback loop controlling the pumps of the respective liquid supply lines. Additionally or alternatively, the apparatus may comprise at least one flow sensor integrated into each of the liquid supply lines upstream of the mixing device, e.g. positioned between the pump and the mixing device, wherein at least one readout provided by said sensor(s) is used as a feedback signal to regulate the activity of one or more of the pumps. Further, at least one readout provided by at least one of the sensor(s) may be used to control whether the liquid flow is directed into the reaction vessel or into the waste container without passage through the reaction vessel. In some embodiments, the number of sensors n is selected from the group consisting of 1, 2, 3, or 4. The skilled person will understand that a variety of sensors may be suitable for this and (s)he will select the appropriate sensor in dependence of the synthesis chemistry envisaged. In some embodiments, the n sensor(s) are independently selected from the group consisting of an infrared spectrometer, a density sensor, a refractometer, a conductivity sensor, a temperature sensor, an impedance sensor, a UV/Vis absorption sensor. In some embodiments, the n sensor(s) are independently selected from the group consisting of an infrared spectrometer, a refractometer, a density sensor, a conductivity sensor, a temperature sensor, an impedance sensor, a UV/Vis absorption sensor, wherein at least one of the n sensors is an infrared spectrometer. In some embodiments, the n sensor(s) are independently selected from the group consisting of an infrared spectrometer, a refractometer, a density sensor, a conductivity sensor, a temperature sensor, an impedance sensor, a UV/Vis absorption sensor, wherein at least one of the n sensors is a density sensor. A further sensor may be integrated into the liquid conduit, which connects the reaction vessel to the waste container. The sensor may be selected from the group consisting of an infrared spectrometer, a density sensor, a refractometer, a conductivity sensor, a temperature sensor, an impedance sensor, a UV/Vis absorption sensor. In one embodiment, the apparatus may comprise a conductivity sensor, a temperature sensor, and a UV absorption sensor, which sensors are positioned downstream of the mixing device and determine at least one property of the liquid emerging from the mixing device.

The liquid supply unit may further comprise at least one heat exchanger. The heat exchanger may positioned between the mixing device and the first of the n sensor(s) (s1 to sn), or it may be part of the mixing device.

The liquid pumps to be integrated into the liquid supply lines are preferably designed such that their reagent-exposed surfaces are inert. It is preferred that at least one of the pumps has a corrosion resistant surface (and thus in particular an "acid-resistant" surface as defined above), e.g. made from Hastelloy alloys or polytetrafluoroethylene. Liquid pumps particularly suitable for use within the liquid supply lines provide a constant flow with minimal pulsation and allow for seamless variation of liquid flow rates. For example, diaphragm pumps may be used. In some embodiments of the present invention, each of the pumps may provide a maximal flow rate of up to 50 L/min, 80 L/min, 100 L/min, 200 L/min, or 300 L/min. In some embodiments, one of the pumps may provide a maximal flow rate of 100 L/min, while the other pump(s) may provide a maximal flow rate of 60 L/min. In one embodiment, the pumps p1, and p2 of a first and a second liquid supply line may provide 10 ml/min, and the pump p3 of a third liquid supply line has a pumping power of about 50 ml/min.

The control unit may control, inter alia, the actions of the pumps and automated valves of the apparatus and receive signals from an operator as well as from the sensors of the system (the n sensor(s) and/or the further sensor). The control unit may comprise several devices, which form different hierarchical levels of control, as is the case for a supervisory control and data acquisition (SCADA) control system architecture. For example, the control unit may comprise one or more remote supervisory computers, which gather data from and send control commands to peripheral devices, and one or more peripheral devices such as remote terminal units (RTU), programmable logic controllers (PLC) and user interfaces such as GUI panels. The PLCs and the supervisory SCADA software may receive input from field sensors such as sensors of temperature, pressure, level, weight, position, or concentration, amongst others. The one or more SCADA supervisory computing platform may additionally interact with a manufacturing execution system (MES), which in turn interacts with an enterprise resource planning (ERP) system. Moreover, the one or more SCADA supervisory computing platform may execute logging tasks by sending specific process parameters, e.g. the sensor data on the composition of the deprotection reagent, to a dedicated database. In some embodiments, the control unit comprises at least one SCADA system and at least one PLC with sensors and actors controlling the actions of the pumps and valves. Alternatively, a local control unit may regulate the function of the pumps in dependence of the signals received from the sensors downstream of the mixing unit. Hence, the local control unit may either be under the supervision of a central control unit, or it may be independent.

The control unit may preferably be configured to control the execution of a synthesis protocol comprising at least two iterations of a coupling cycle, wherein the protocol individually defines the composition of an acidic deprotection reagent for each coupling cycle and wherein the control unit accordingly directs reagent flow through the at least one liquid supply line, the inner surface of which is made from an acid-resistant material. The control unit may allow the user to define the sequence of process steps and in particular the composition of the coupling reagent for each coupling cycle. When executing this synthesis protocol, the control unit may direct the action of the valves and pumps so as to achieve a specific composition of the deprotection reagent in each of the coupling cycles and may control said compositions by means of the signals from the field sensors obtained, e.g. from the flow sensors upstream of the mixing device, or from the sensors positioned between the mixing device and the reaction vessel.

In some embodiments, the apparatus according to the present invention—or at least the exposed surfaces thereof—is/are made of a material, which is essentially inert against the reagents it will be exposed to. In some embodiments, the apparatus—or at least the exposed surfaces thereof—is/are made of stainless steel, Hastelloy® alloys, or polymer-coated metal. Preferably, the material is compliant with the applicable regulations for the production of pharmaceutical products, cosmetics and/or food and beverages, i.e. it complies with good manufacturing practices (GMP). In some embodiments, at least the exposed surfaces of the mixing device and one line of the apparatus—i.e. one liquid conduit comprising one or more liquid inlets, valves, and a pump, wherein the liquid conduit ends at the inlet of the mixing device—are made from an acid resistant material such as an acid resistant alloy or an acid resistant polymeric coating, while other parts of the apparatus are made from stainless steel.

The operation of an apparatus according to the present invention may involve the steps detailed below. Although the steps will be explained with reference to FIG. 4 for illustration, this is not to be interpreted as limiting the teachings to the specific apparatus of FIG. 4. Moreover, it is to be understood that other reagents may be used, depending on the synthetic strategy. The following sequence of steps is hence a mere example for one possible routine within one specific coupling cycle.

1) Setup liquid supply lines

| line | vessel | content |
|------|--------|---------|
| 1 | v1-1 | Process solvent, e.g. acetonitrile |
| 1 | v1-2 | acetic anhydride |
| 1 | v1-3 | Dichloroacetic acid |
| 1 | v1-4 | Concentrated solution of iodine dissolved in pyridine |

-continued

| line | vessel | content |
|------|--------|---------|
| 4 | v4-1 | Process solvent, e.g. acetonitrile |
| 4 | v4-2 | N-methylimidazole (NMI) |
| 4 | v4-3 | solution of acidic azole catalyst in anhydrous acetonitrile (ACN) |
| 4 | v4-4 | stock solution of Phenylacetyl disulphide (PADS) in solvent, e.g.pyridine |
| 4 | v4-5 | water |
| 3 | v3-1 | Process solvent, e.g. acetonitrile |
| 3 | v3-2 | protected nucleoside phosphoramidite 1 in anhydrous ACN |
| | . . . | |
| 3 | v3-(n-1) | protected nucleoside phosphoramidite (n-1) in anhydrous ACN |
| 3 | v3-n | Pyridine (or an alternative weak base) |
| 2 | v2-1 | anhydrous ACN |
| 2 | v2-2 | toluene |

Of note, all vessels comprise pure liquids, unless they contain reagents, which are solid under ambient temperature and need to be provided as stock solutions.

2) Prepare detritylation solution

Liquid flow from vessels v1-3 and v2-2 into the mixing device 5. Flow is directed into waste container 7 at first, and directed to the reaction vessel (6) as soon as the intended mixture is obtained.

3) Flush lines 1 and 2, the mixing chamber, and the reaction vessel with acetonitrile from vessels v1-1 and v2-1.

4) Prepare coupling solution with protected nucleoside phosphoramidite 1

Liquid flow from vessels v3-2, and v4-3 into the mixing device 5. Flow may be directed into waste container 7 at first, and is directed to the reaction vessel 6 as soon as the intended mixture is obtained. Recycle the coupling solution from the liquid conduit 9 via line 4 and mixing device 5 into the reaction vessel 6.

5) Flush lines 2, 3, and 4, the mixing chamber, and the reaction vessel with acetonitrile from vessels v2-1, v3-1 and v4-1.

6) Prepare oxidation solution

Liquid flow from vessels v1-4, v4-5, and v3-n into the mixing device 5. Flow is directed into waste container 7 at first, and directed to the reaction vessel 6 as soon as the intended mixture is obtained.

Alternatively: Prepare sulfurization solution

Liquid flow from vessels v4-4, and v3-n into the mixing device 5. Flow is directed into waste container 7 at first, and directed to the reaction vessel 6 as soon as the intended mixture is obtained.

Recycle via line 2 during reaction.

7) Flush lines 2 and 1, 4, 3 (oxidation) or 4, 3 (sulfurization) the mixing chamber, and the reaction vessel with acetonitrile from vessels v2-1, v1-1, 4-1 and v3-1 (oxidation), or v2-1, v4-1 and v3-1 (sulfurization).

8) Prepare blocking (aka. capping) solution

Liquid flow from vessels v1-2, v4-2, v3-n, and v2-1 into the mixing device 5. Flow is directed into waste container 7 at first, and directed to the reaction vessel 6 as soon as the intended mixture is obtained. ecycle during reaction vial line 2.

9) Flush lines 1, 2, 3, and 4, the mixing chamber, and the reaction vessel with acetonitrile from vessels v1-1, v2-1, v3-1, and v4-1.

As can be seen from the steps above, all reagents may be mixed from pure liquids, unless the starting materials are not liquid and need to be provided as solutions. Apart from procedural advantages, this increases the stability of the reagents used and hence process stability.

Further herein disclosed are advantageous methods of oligomer synthesis using an apparatus as detailed above, wherein at least one solution independently selected from the group consisting of the deprotection solution, the oxidizing and the sulfurization solution is prepared by in-line mixing. In further advantageous methods of oligomer synthesis using an apparatus as detailed above, at least two solutions independently selected from the group consisting of the deprotection solution, the blocking solution, the oxidizing and the sulfurization solution are prepared by in-line mixing. In other embodiments, at least three solutions independently selected from the group consisting of the deprotection solution, the blocking solution, the oxidizing and the sulfurization solution are prepared by in-line mixing.

The apparatus of the present invention may be used to execute a protocol for the synthesis of an oligonucleotide comprising at least two iterations of a coupling cycle, wherein the protocol individually defines the composition of an acidic deprotection reagent for each coupling cycle.

The explanations and definitions set out above with respect to the apparatus of the present invention are likewise applicable with respect to the methods of the present invention, and vice versa. Preferably, the methods are is carried out in automated fashion.

As used herein, the expression "in automated fashion" describes a process, which is routinely executed without the intervention and without the permanent control by a human being. This may mean that the steps of the synthesis process are governed by a control unit as detailed above. However, the apparatus and/or control unit may be configured so as to allow for or even request the intervention by a human being under specific circumstances. This may occur, e.g., in case of unforeseen events, such as process parameters being outside of specific predefined ranges. Moreover, it may be advantageous to be able and carry out, e.g., a certain number of coupling cycles in automated fashion, while executing a specific critical step under human control and/or with human intervention.

The steps of the methods detailed herein may be executed in the exact order, in which they are recited. However, the skilled person is aware of the fact that the order of steps may be different in some cases. As used herein, the expression "the following steps 1 to x are carried out" refers to a process, where each of the steps 1 to x are carried out, although not necessarily in the order indicated.

As used herein, the expressions "coupling cycles", "cycles of building block addition", "cycle of the iterative polymer synthesis process", "elongation cycle" and "synthetic cycle" are synonyms and relate to the steps needed to extend a polymeric chain, e.g. a oligonucleotide chain, by one building block during synthesis. Typically, one synthetic cycle involves at least one a step of providing an unprotected polymeric chain for coupling, and a step of coupling the building block to the polymeric chain. The step of providing the unprotected polymeric chain may involve removal of a temporary protecting group, separation, and washing of the polymeric chain.

In one preferred embodiment, the present invention relates to a method of assembling an oligonucleotide chain in automated fashion by repeated cycles of building block coupling, wherein the following steps 1 through 6 are carried out anew in each of the cycles of building block coupling:

1. Providing a n-mer oligonucleotide, where n is an integer equal to or larger than 1, bound to a solid support and comprising a first reactive group free to extend the oligonucleotide backbone by reaction with a second reactive group comprised in a building block to be incorporated;

2. Providing the building block to be incorporated, which comprises the second reactive group free to react with the first reactive group of the n-mer oligonucleotide, and which further comprises a first reactive group blocked by an acid sensitive temporary protecting group;

3. Contacting the n-mer oligonucleotide with the building block to be incorporated under conditions that allow for binding of the first reactive group of n-mer oligonucleotide to the second reactive group of the building block to be incorporated, and generating a protected, extended n-mer oligonucleotide, which is blocked from further extension by the acid sensitive temporary protecting group;

4. Preparing an acidic deprotection reagent by mixing at least two liquid compositions;

5. Contacting the protected, extended n-mer oligonucleotide of step 3 with the acidic deprotection reagent of step 4, thereby cleaving the acid sensitive temporary deprotecting group from the extended n-mer oligonucleotide; and 6. Removing the deprotection reagent and soluble cleavage product from the extended n-mer oligonucleotide, which may then be used as the n-mer oligonucleotide in step 1 of the following coupling cycle.

The above expression "providing a n-mer oligonucleotide" may be understood in the broadest possible sense. At the beginning of the reaction, step 1 may involve providing a nucleoside, which is immobilized to a solid support and carries an acid sensitive temporary protecting group blocking backbone extension. Some of such immobilized nucleosides are commercially available. The temporary protecting group may then be removed by incubation with an acidic deprotection reagent, followed by draining/washing steps to provide the n-mer oligonucleotide. In other cases, the assembly of the oligonucleotide chain may already start with a longer oligonucleotide bound to a solid support. Between coupling cycles, step 1 may partially overlap with steps 5 and 6 of the antecedent coupling cycle, namely with the cleavage of the temporary protecting group from the extended n-mer oligonucleotide, and may comprise further rinsing steps in order to condition the deprotected, extended n-mer oligonucleotide of the antecendent coupling cycle for use in the following coupling cycle.

The skilled person is well aware of the fact that numerous solid supports may be used for oligonucleotide synthesis, including supports made from controlled pore glass (CPG) and crosslinked polystyrene beads. Linkers for attaching the first oligonucleotide to the solid support are likewise well known in the art. When synthesizing oligonucleotides with a backbone from monosaccaride moieties linked by phosphodiester bonds, the first reactive group may be a hydroxyl group, preferably a primary hydroxyl group such as, e.g., the 5' hydroxyl group of the ribose moiety. However, the first reactive group may be any reactive group involved in forming the backbone of the oligonucleotide structure at hand.

As used herein, the expression "oligonucleotide backbone" may be used to refer to the repeating chain of phosphodiester bonds/phosphodiester bond analogs and ribose/ribose analog moieties, which provide a scaffold, to which the nucleobases/nucleobase analogs are linked. The first reactive group may typically be located at one end of the oligonucleotide backbone and the second reactive group may be located on the other end of the oligonucleotide The expression "providing a building block" may be understood in the broadest possible sense. The building block to be incorporated may comprise any nucleoside or nucleoside analog, which is to be incorporated into the oligonucleotide chain. It may comprise an abasic site, a nucleobase, or a nucleobase analog bound via a glycosidic bond or an analog of such a bond. The building block may be monomeric or may be oligomeric, i.e. the building block may be an oligonucleotide itself. The building block may further comprise a non-nucleosidic modification such as cholesterol. The building block comprises a second reactive group free to react with the first reactive group of the n-mer oligonucleotide. The second reactive group may be a phosphoramidite group, e.g. a 3'-O—(N,N-diisopropyl phosphoramidite) group, or a H-phosphonate monoester. Moreover, the building block comprises a first reactive group, which is blocked from reaction by a temporary protective group. The first reactive group comprised in the building block is the same chemical moiety as present on the n-mer oligonucleotide in the equivalent location. The acid sensitive protecting group, which blocks the first reactive group of the building block, may be a trityl type protecting group, for example triphenylmethyl (trityl), 4-monomethoxytrityl (MMT), 4,4'-dimethoxytrityl (DMT), 9-phenylxanthen-9-yl (pixyl) or 9-(p-methoxyphenyl)xanthine-9-yl (MOX).

In some embodiments, the first reactive group is a hydroxyl group, preferably a primary hydroxyl group, e.g. the 5' hydroxyl group of a ribose/ribose analog moiety, and the second reactive group is a phosphoramidite group, e.g. a 3'-O—(N,N-diisopropyl phosphoramidite) group. In further embodiments, the first reactive group is a hydroxyl group, preferably a primary hydroxyl group, e.g. the 5' hydroxyl group of a ribose/ribose analog moiety, and the second reactive group is a phosphonate monoester group.

The skilled person is well aware of the conditions needed to make the first reactive group of the n-mer oligonucleotide react with the second reactive group of the building block. For example, the formation of a phosphite triester group may be induced by contacting the n-mer oligonucleotide with the building block in anhydrous solvent, commonly acetonitrile, using an acidic azole catalyst, such as 1H-tetrazole, 5-ethylthio-1H-tetrazole. The protected, extended n-mer may then be produced by exposing the phosphite triester group to a sulfurizing reagent, or an oxidizing reagent, as is standard in the art. As a further example, pivaloyl chloride, 2,4,6-triisopropylbenzenesulfonyl chloride (TPS-Cl), and other compounds may be used as activators when the second reactive group is a phosphonate monoester group.

The present method foresees to prepare the acidic deprotection reagent anew in each coupling cycle by mixing at least two liquid compositions. Hence, the composition of the deprotection reagent may be defined individually for each coupling cycle. This allows to adjust, e.g., the content of acid to the specific circumstances encountered in the respective coupling cycle. For example, purine bases may be more easily cleaved off the oligonucleotide than pyrimidine bases, leaving an abasic site. The so-called depurination occurs more easily at the ends of the oligonucleotide strand than in its middle. It is therefore advantageous to be able to optimize the conditions for removal of the temporary protecting group at each step. The protocol thereby allows to minimize unwanted side reactions and to maximize the purity of the raw oligonucleotide chain assembled during synthesis.

In some methods according to the present invention, the composition of the deprotection reagent is different between at least two coupling cycles. The composition of the deprotection reagent may in particular differ with respect to the amount of acid contained. For example, the concentration of acid may increase with cycle number. In one embodiment, the content of acid in the deprotection reagent is selected form the range of 0.1% (w/w) to 50% (w/w) acid individually for each coupling cycle. For example, the concentration of acid in the deprotection reagent may be 0.1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% (w/w). In many cases, the concentration of acid in the deprotection reagent may be selected from the range of 0.5 to 20% DCA. The acid contained in the deprotection reagent may be selected from DCA and TCA, and preferably be DCA. The content of acid in the deprotection reagent may be selected form the range of 0.1% (w/w) to 50% (w/w) DCA in solvent individually for each coupling cycle. The content of acid in the deprotection reagent may be selected form the range of 0.1% (w/w) to 20% (w/w) TCA in solvent individually for each coupling cycle. A preferred solvent is toluene.

The deprotection reagent may be prepared by blending flows of pure DCA and solvent inside the mixing device of the present apparatus. Alternatively to the pure acid, concentrated solutions of the respective acid in solvent may be used and may be diluted further by mixing with a sequent liquid, e.g. with solvent. For example, a solution of 50% DCA in toluene may be provided as a stock solution and may be blended with toluene to achieve the intended concentration. Alternatively, a solution of TCA may be used. While the deblocking solution is typically made by diluting an acid such as DCA in a solvent such as toluene, the deprotection reagent may comprise further components such as cation scavenger. The deprotection reagent may be removed after completing the deprotection reaction by draining from the solid support, and/or by washing steps. It may be replaced by flushing with process solvent, e.g. acetonitrile.

The following aspects of the invention are likewise disclosed:

1. An apparatus for the synthesis of oligomers, comprising:
   a) a reaction vessel connected via a liquid conduit to a waste container;
   b) a liquid supply unit for delivering liquid reagents to the reaction vessel;
   c) a bypass conduit, which allows to direct liquid flow from the liquid supply unit into the waste container without passage through the reaction vessel; and
   d) a main control unit
   characterized in that the liquid supply unit comprises:
   b-1) at least one mixing device, connected to
   b-2) at least 4 upstream liquid lines, each comprising one liquid conduit with n liquid inlets, where n is an integer between 1 and 25, and one liquid pump; and
   b-3) n sensors, where n is an integer equal to or bigger than 1, which sensor(s) is/are positioned downstream of the mixing device and determine(s) at least one property of the liquid emerging from the mixing device, wherein at least one readout provided by the sensor(s) is used as a feedback signal to regulate the activity of one or more of the liquid pumps.

2. The apparatus according to aspect 1, wherein the main control unit receives input from the n sensor(s) and adjusts the liquid flow from one or more of the pumps.

3. The apparatus according to any one of aspects 1 or 2, wherein the pumps are controlled by a local control unit receiving input from the sensor(s).

4. The apparatus according to any one of aspects 1 to 3, wherein the mixing device is connected via a liquid conduit to the reaction vessel.

5. The apparatus according to any one of aspects 1 to 3, wherein the mixing device is connected via a liquid conduit to a manifold, which manifold is connected via a liquid conduit to the reaction vessel.

6. The apparatus according to aspect 5, wherein the manifold is further connected to at least one liquid conduit providing influx from a liquid inlet by means of a liquid pump.

7. The apparatus according to any one of aspects 1 to 6, wherein the liquid supply unit further comprises at least one heat exchanger, preferably wherein at least one of the heat exchanger(s) is positioned between the mixing unit and first of the n sensor(s).

8. The apparatus according to any one of aspects 1 to 7, wherein the reaction vessel is a packed reactor column or a batch reactor.

9. The apparatus according to any one of aspects 1 to 8, wherein the inner surfaces of mixing device and at least one of the liquid lines are made from a corrosion-resistant material, preferably from Hastelloy alloy or from polytetrafluoroethylene.

10. The apparatus according to any one of aspects 1 to 9, wherein the n sensor(s) are independently selected from the group consisting of an infrared spectrometer, a density sensor, a refractometer, a conductivity sensor, a temperature sensor, an impedance sensor, a UV/Vs absorption sensor.

11. The apparatus according to any one of aspects 1 to 10, further comprising a recycling circuit directing flow from the liquid conduit via the mixing unit and the n sensor(s) into the reaction vessel by means of a pump.

12. The apparatus according to any one of aspects 1 to 10, further comprising a recycling circuit directing flow from the liquid conduit via the mixing unit and the n sensor(s) into the reaction vessel by means of a pump, wherein one of the liquid lines with the pump of said liquid line is connected via one of its inlets and a three way valve to the liquid conduit and functions as the recycling line.

13. An apparatus for the solid phase synthesis of oligonucleotides, characterized in that the apparatus comprises a batch reactor for carrying out the synthesis inside said batch reactor.

14. A method for the synthesis of oligonucleotides using an apparatus according to any one of aspects 1 to 13.

15. The method according to aspect 14, wherein at least two solutions independently selected from the group consisting of a deprotection solution, a blocking solution, an oxidizing and a sulfurization solution are prepared by in-line mixing in a liquid line.

The following figures and their descriptions are provided for illustrative purposes only and are not to be construed as limiting the scope of the claims.

BRIEF DESCRIPTION OF THE FIGURES

The figures show

| List of reference signs | |
| --- | --- |
| 1 | liquid supply line 1 |
| i1-1 | inlet no. 1 of line 1 |
| i1-2 | inlet no. 2 of line 1 |
| i1-3 | inlet no. 3 of line 1 |
| i1-4 | inlet no. 4 of line 1 |
| i1-n | inlet no. n of line 1 |
| p1 | liquid pump of line 1 |
| l1 | liquid conduit of line 1 |
| 2 | liquid supply line 2 |
| i2-1 | inlet no. 1 of line 2 |
| i2-2 | inlet no. 2 of line 2 |
| i2-3 | inlet no. 3 of line 2 |
| i2-4 | inlet no. 4 of line 2 |
| i2-n | inlet no. n of line 2 |
| p2 | liquid pump of line 2 |
| l2 | liquid conduit of line 2 |
| 3 | liquid supply line 3 |
| i3-1 | inlet no. 1 of line 3 |
| i3-2 | inlet no. 2 of line 3 |
| i3-3 | inlet no. 3 of line 3 |
| i3-4 | inlet no. 4 of line 3 |
| i3-n | inlet no. n of line 3 |
| p3 | liquid pump of line 3 |
| l3 | liquid conduit of line 3 |
| 4 | liquid supply line 4 |
| i4-1 | inlet no. 1 of line 4 |
| i4-2 | inlet no. 2 of line 4 |
| i4-3 | inlet no. 3 of line 4 |
| i4-4 | inlet no. 4 of line 4 |
| i4-n | inlet no. n of line 4 |
| p4 | liquid pump of line 4 |
| l4 | liquid conduit of line 4 |
| v1-n | storage vessel no n of line 1 |
| v2-n | storage vessel no n of line 2 |
| v3-n | storage vessel no n of line 3 |
| v4-n | storage vessel no n of line 4 |
| 5 | mixing device |
| 6 | reaction vessel |
| 7 | waste container |
| 8 | control unit |
| 9 | controllable liquid conduit |
| 10 | valve |
| 11 | bypass conduit |
| s1 | sensor 1 |
| s2 | sensor 2 |
| sn | sensor n |
| 12 | 3 way valve |
| 13 | heat exchanger |
| 14 | manifold |
| 15 | local control unit |

-continued

| List of reference signs | |
| --- | --- |
| 16 | liquid recycling conduit |
| 17 | liquid pump |
| 18 | liquid inlet |
| 19 | liquid supply unit |
| 20 | liquid conduit between mixing device and reaction vessel |
| 21 | liquid conduit between mixing device and manifold |
| 22 | liquid conduit between manifold and reaction vessel |
| 23 | sensor |
| 24 | flow sensor |

DESCRIPTION OF THE FIGURES

Figure 1:
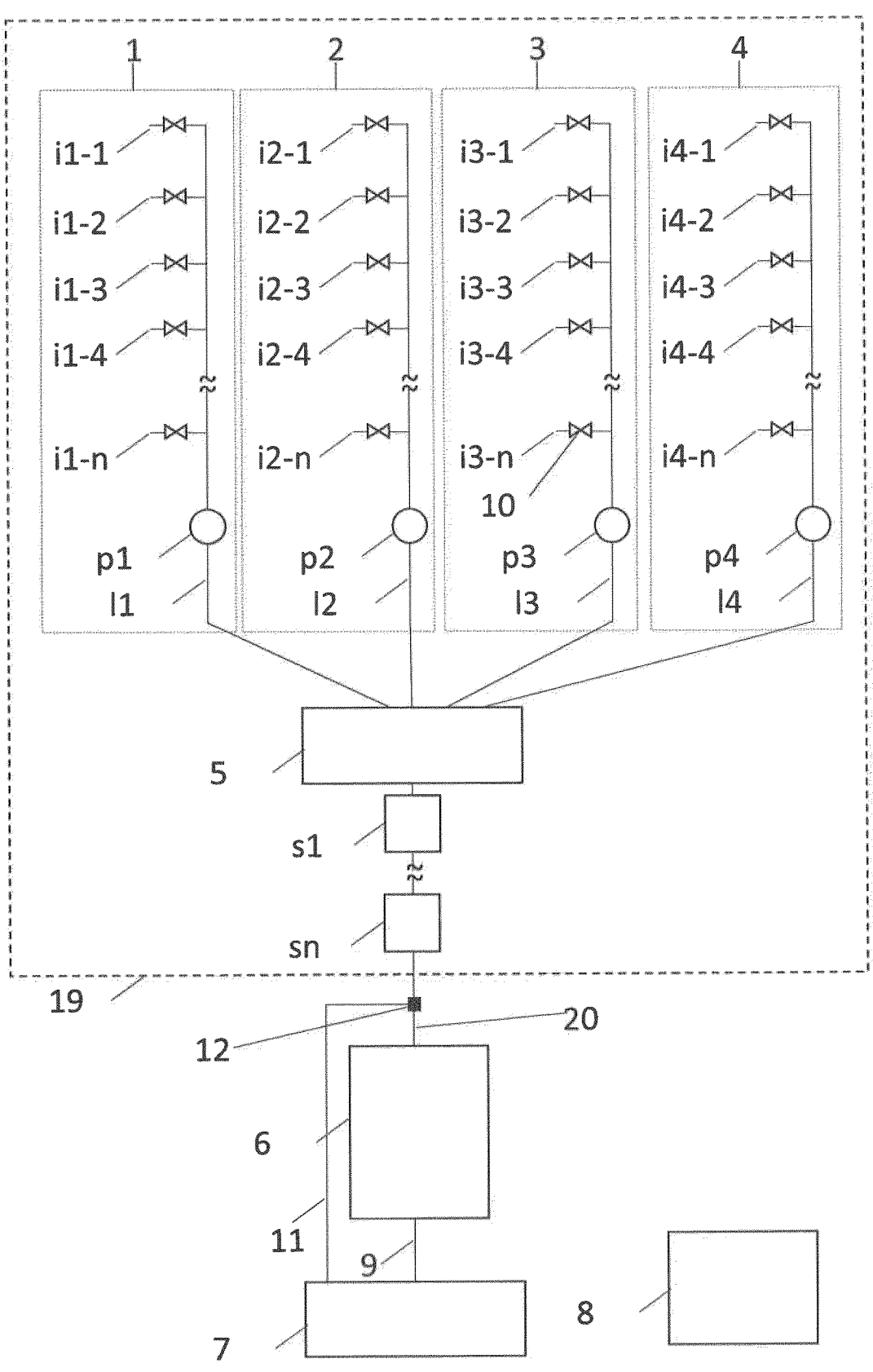
FIG. 1 a basic embodiment of an apparatus for the automated synthesis of oligomers having four liquid supply lines, FIG. 2 a further embodiment of the apparatus additionally comprising a recycling conduit, FIG. 3 a further embodiment of the apparatus where one of the liquid supply lines serves as recycling circuit, FIG. 4 a further embodiment of the apparatus having storage vessels, FIG. 5 another embodiment of the apparatus comprising a manifold, FIG. 6 another embodiment of the apparatus comprising two mixing devices and a manifold, FIG. 7 a further embodiment of the apparatus having two liquid supply lines, FIG. 8 another embodiment of the apparatus having two liquid supply lines and a recycling circuit, FIG. 9 an embodiment of the apparatus of FIG. 7 with additional sensors arranged downstream of the mixing device, FIG. 10 an embodiment of the apparatus of FIG. 3 with only two liquid supply lines, FIG. 11 an embodiment of the apparatus of FIG. 2 with only three liquid supply lines, FIG. 12 another embodiment of the apparatus having three liquid supply lines, wherein one of the liquid supply lines serves as recycling circuit, and FIG. 13 a further embodiment of the apparatus of FIG. 3 with only three liquid supply lines.

FIG. 1 shows a basic embodiment of the apparatus according to the present invention. The liquid supply unit 19 of the apparatus may comprise a mixing device 5, which is connected to four liquid supply lines, a first liquid supply line 1, a second liquid supply line 2, a third liquid supply line 3 and a fourth liquid supply line 4. Each of said liquid supply lines comprises a pump [(p1), (p2), (p3), or (p4), respectively], a liquid conduit [(l1), (l2), (l3), or (l4), respectively], and n inlets [(i1-1 to i1-*n*), (i2-1 to i2-*n*), (i3-1 to i3-*n*), (i4-1 to i4-*n*), respectively], where n is an integer equal to or greater than 1. The fluid connection between each of the liquid inlets and the conduit may be regulated by means of a valve 10. The liquid supply lines 1, 2, 3, 4 are highlighted by dashed boxes for the sake of clarity. It is understood that the entire length of the liquid conduits [(l1), (l2), (l3), or (l4), respectively] up to the inlet of the mixing device 5 is considered as belonging to the respective liquid supply line. The mixing device 5 unites any flows from said liquid supply lines 1, 2, 3, 4 and mixes them so as to obtain one homogenous solution, which may be led though a liquid conduit 20 comprising n sensors (s1 to sn), where n is an integer equal to or greater than 1, into the reaction vessel 6. The sensors may provide a feedback signal correlating with the composition of the solution to a control unit 8, which signal is used by the control unit 8 to regulate the flow of the line's pumps [(p1), (p2), (p3), or (p4), respectively]. As long as the composition of the solution passing the sensors is not stable within a given set interval, the solution will not be directed into the reaction vessel, but will be guided via an automated three way valve 12 and a bypass conduit 11 into a waste container 7. Further to the pumps p1, p2, p3, p4, the control unit 8 controls the liquid flow through the conduits 11, 20, and through the liquid conduit 9 connecting the reaction vessel with the waste container 7. The control unit 8 may thereby determine which solution is incubated for which duration of time with the contents of the reaction vessel.

Figure 2:
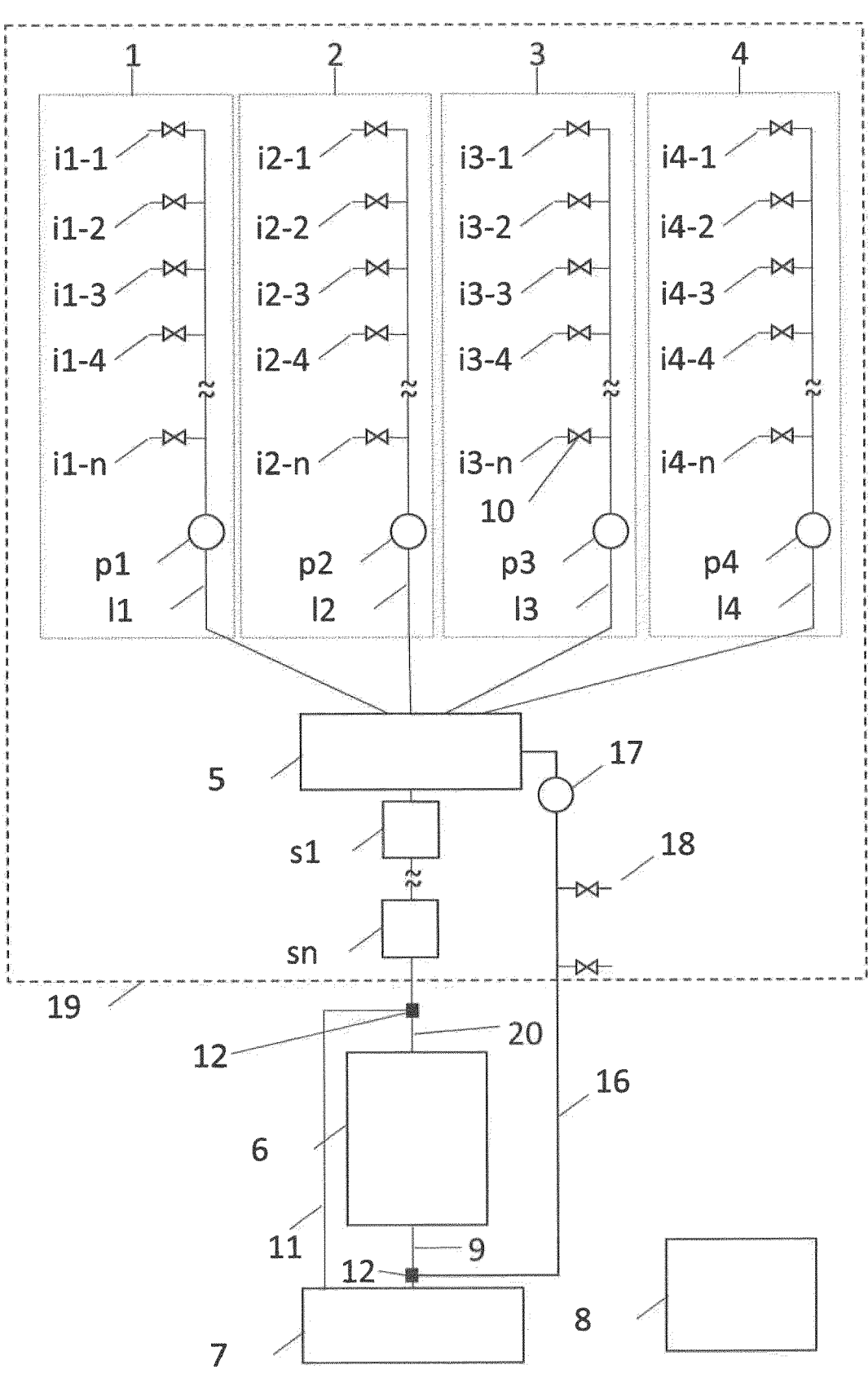

FIG. 2 shows a further embodiment of the inventive apparatus, to which all of the remarks re. FIG. 1 apply. In addition to the above-discussed elements, a liquid recycling conduit 16 with a pump 17 is connected to the liquid conduit 9 via a three way valve 12. This setup allows to circulate a given solution coming out of the reaction vessel 6 via the mixing device 5 and the liquid conduit 20 with the n sensors (s1 to sn) back into the reaction vessel 6. The actions of the three-way valve 12 and of the pump 17 are controlled by the control unit 8. Additional liquid inlets 18 on the recycling conduit 16 allow for flexibility.

Figure 3:
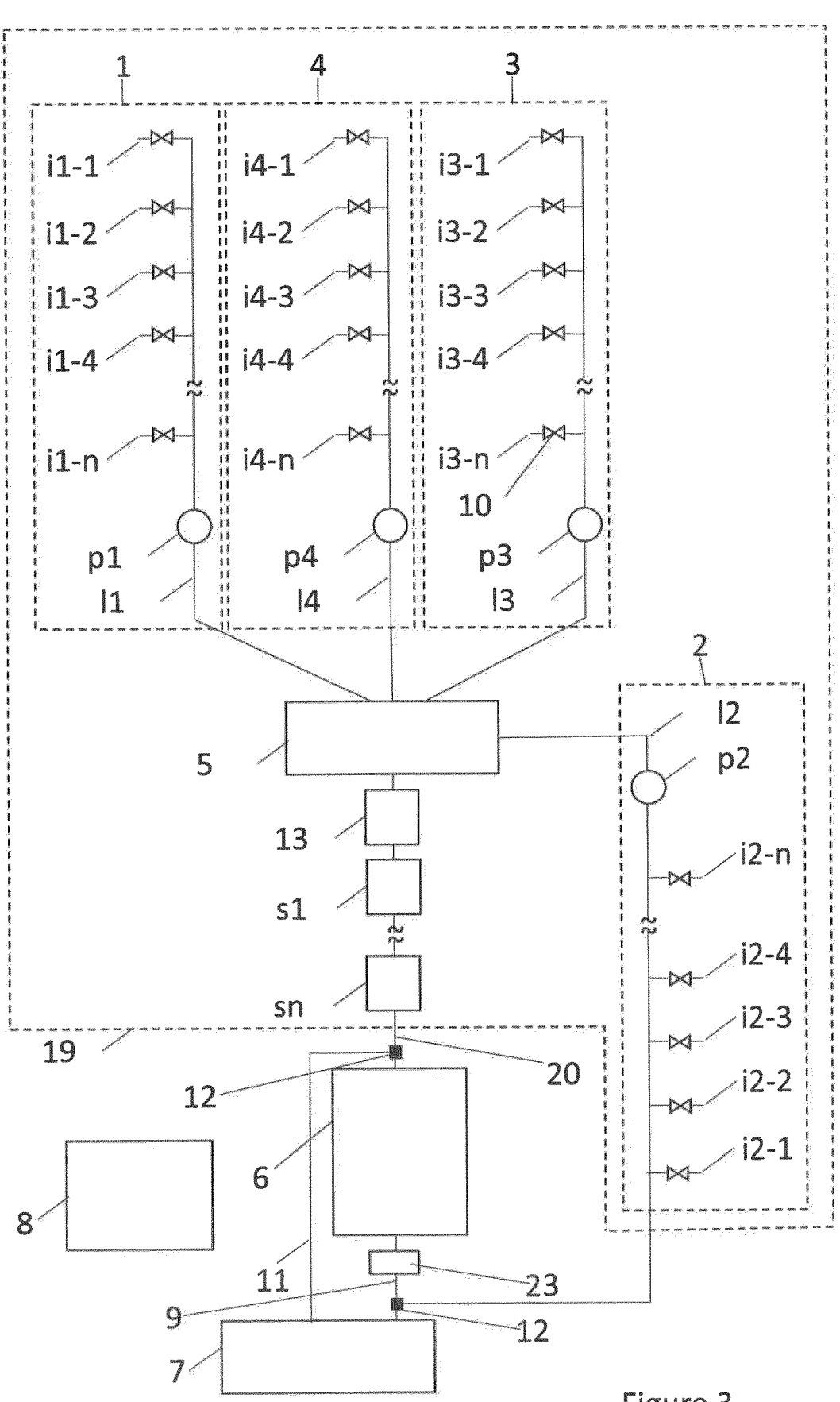

FIG. 3 shows a further embodiment of the inventive apparatus, to which all of the remarks re. FIG. 1 apply. In addition to the above-discussed elements, a heat exchanger 13 is integrated into the liquid conduit 20 between the mixing device 5 and the first sensor s1. This allows to regulate the temperature of the solution in order to obtain more reliable readouts from the sensors and to regulate the temperature of the reagents within the reaction vessel 6. Moreover, a further sensor 23 is integrated into the liquid conduit 9 downstream from the reaction vessel. This sensor likewise provides a signal to the control unit, which may correlate with events inside the reaction vessel. The second liquid supply line 2 in this embodiment serves a double function in that one of its inlets is connected to the liquid conduit 9 via a three way valve 12 positioned between the sensor 23 and the waste container 7. This setup allows to circulate a given solution coming out of the reaction vessel 6 via the liquid conduit 12, the mixing device 5 and the liquid conduit 20 with the n sensors (s1 to sn) back into the reaction vessel 6, but without the need for a dedicated recycling conduit and pump as shown in FIG. 2. The actions of the three-way valve 12 and of the pump p2 are controlled by the control unit 8.

Figure 4:
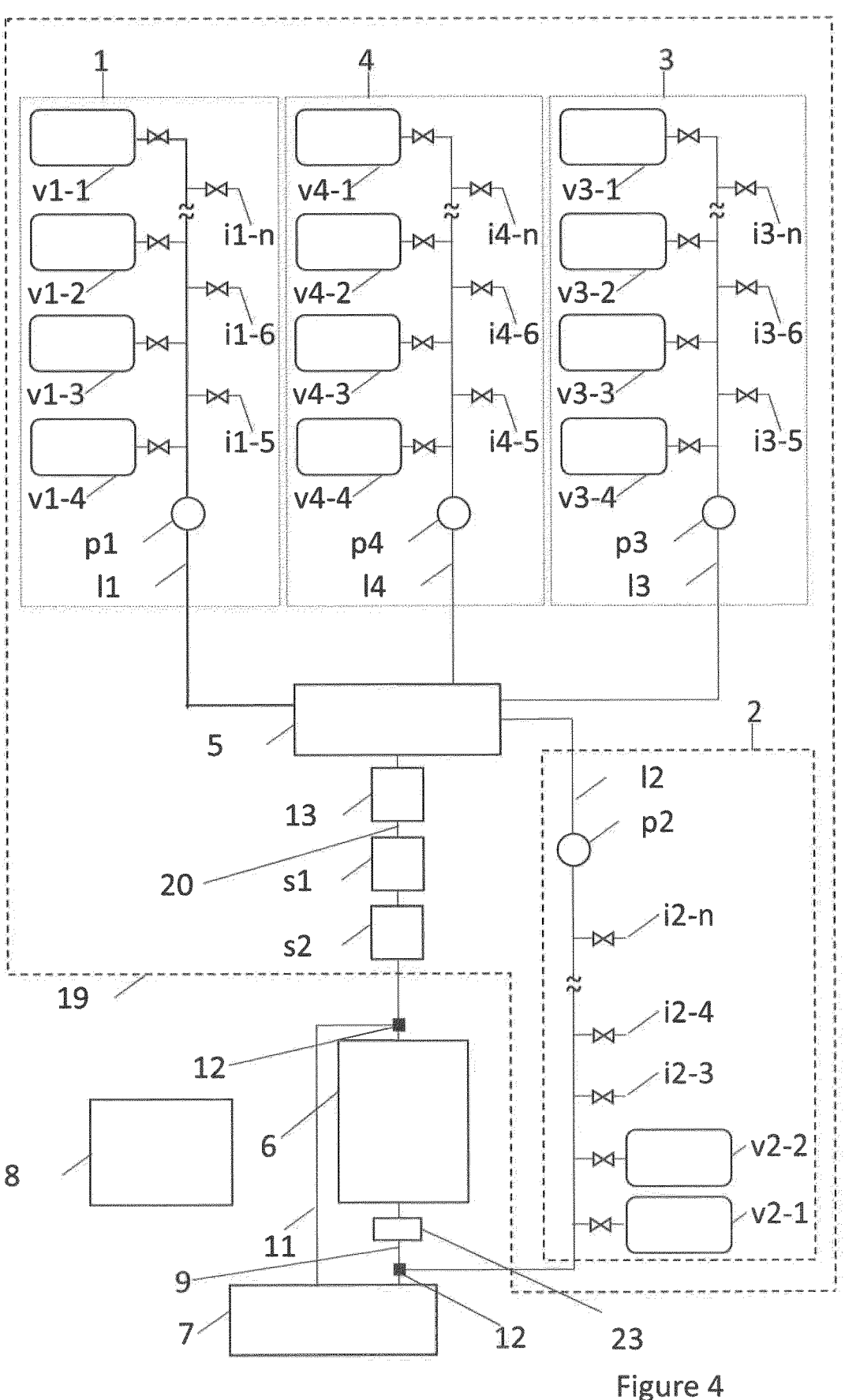

FIG. 4 shows a further embodiment of the inventive apparatus, to which all of the remarks re. FIG. 3 apply. Three liquid supply lines 1, 3, 4 are shown with four storage vessels each [(v1-1 to v1-4), (v3-1 to v3-4), (v4-1 to v4-4), respectively] and n–4 inlets [(i1-5 to i1-$n$), (i3-5 to i3-$n$), (i4-5 to i4-$n$), respectively], where n is an integer equal to or greater than 7. The second liquid supply line 2 serves a double function of liquid supply line and recycling conduit as explained with reference to FIG. 3 above. It is shown with two storage vessels (v2-1), (v2-2) and n–2 inlets (i2-3 to i2-$n$), where n is an integer equal to or greater than 5. The liquid supply unit 19 comprises a heat exchanger 13 and two sensors (s1), (s2).

Figure 5:
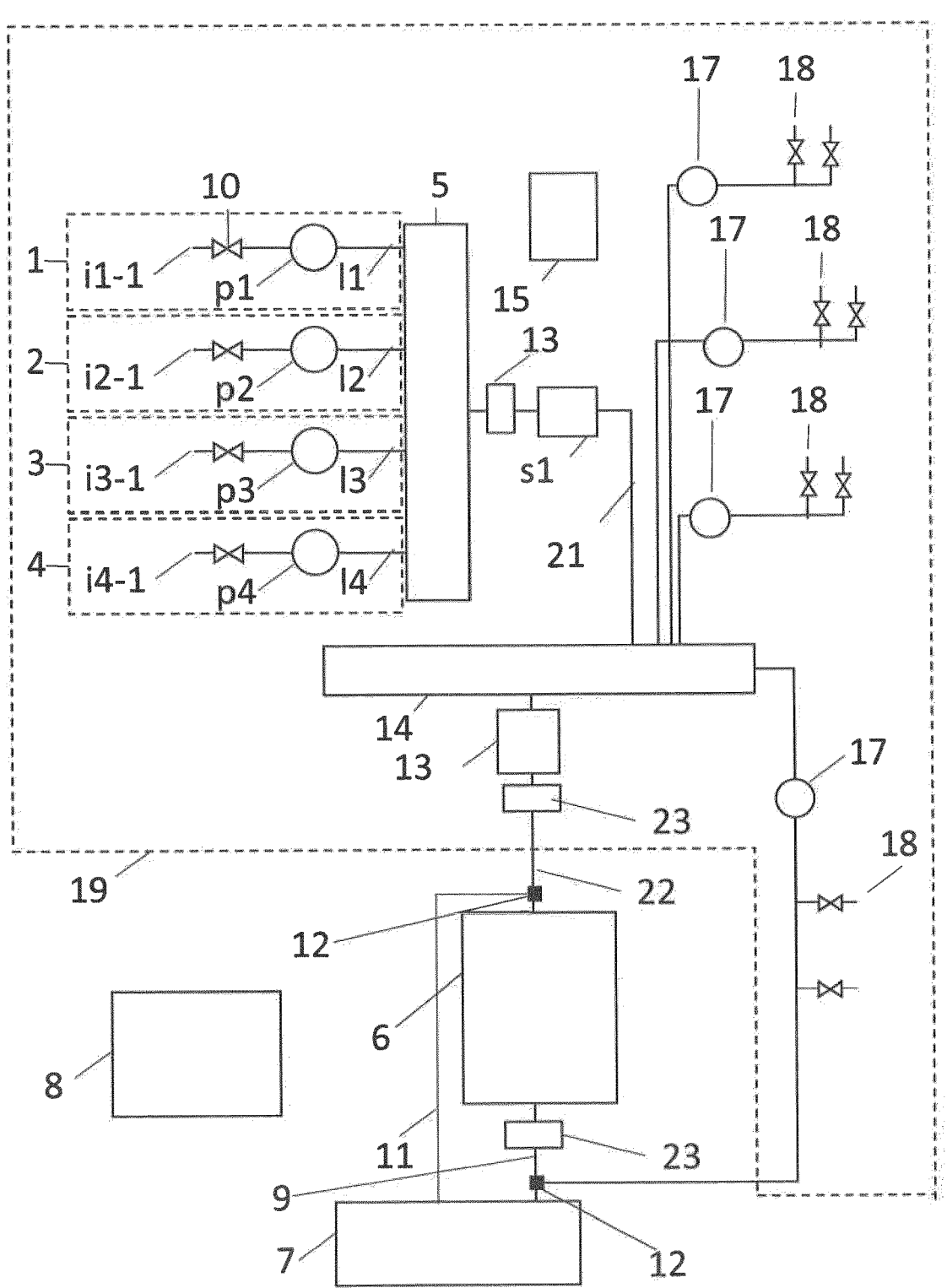

FIG. 5 shows a further embodiment of the inventive apparatus. The liquid supply unit 19 of the apparatus may comprise a mixing device 5, which is connected to four liquid supply lines 1, 2, 3, 4. Each of said liquid supply lines comprises a pump [(p1), (p2), (p3), or (p4), respectively], a liquid conduit [(l1), (l2), (l3), or (l4), respectively], and n inlets [(i1-1 to i1-$n$), (i2-1 to i2-$n$), (i3-1 to i3-$n$), (i4-1 to i4-$n$), respectively], where n is an integer equal to or greater than 1. The fluid connection between each of the liquid inlets and the conduit may be regulated by means of a valve 10. The combined solution emerging from the mixing device 5 is directed via a liquid conduit 21 into a manifold 14. Integrated into said liquid conduit 21 are a heat exchanger 13 and a sensor (s1). The sensor (s1) provides signals to a local control unit 15, which regulates the action of the liquid supply line's pumps (p1), (p2), (p3), or (p4). The local control unit 15 may be under the control of the control unit 8, or it may be independent. The manifold 14 is further connected to four additional liquid conduits, each comprising a pump 17 and two liquid inlets 18. The liquid flow emerging from the manifold is directed through a liquid conduit 22 into the reaction vessel 6. An additional heat exchanger 13 and a sensor 23 are integrated into said liquid conduit 22. All other elements are as set out with respect to FIG. 3.

Figure 6:
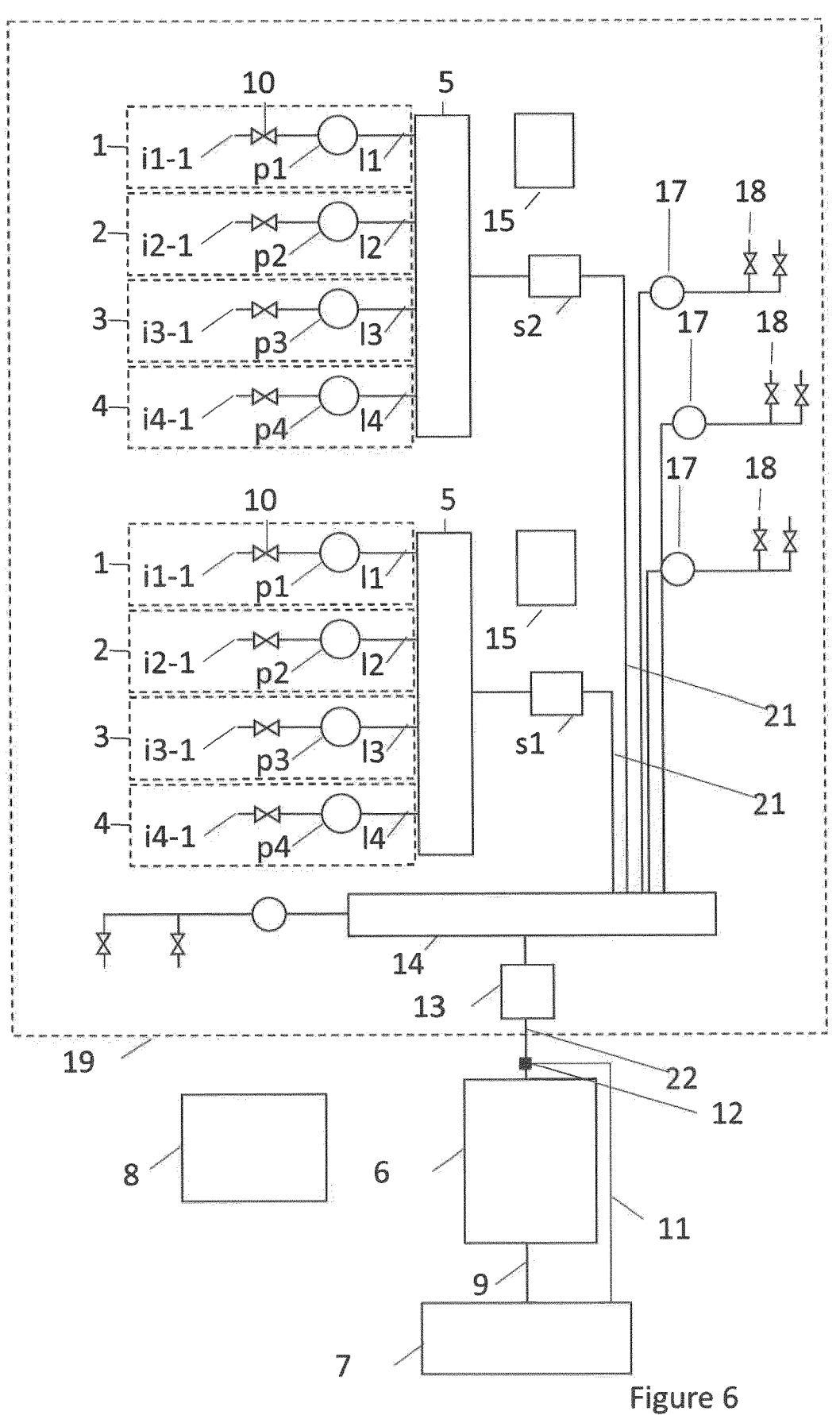

FIG. 6 shows a further embodiment of the inventive apparatus, which is similar to that of FIG. 5. The manifold 14 receives input from two mixing devices 5, each connected to four liquid supply lines 1, 2, 3, 4.

Figure 7:
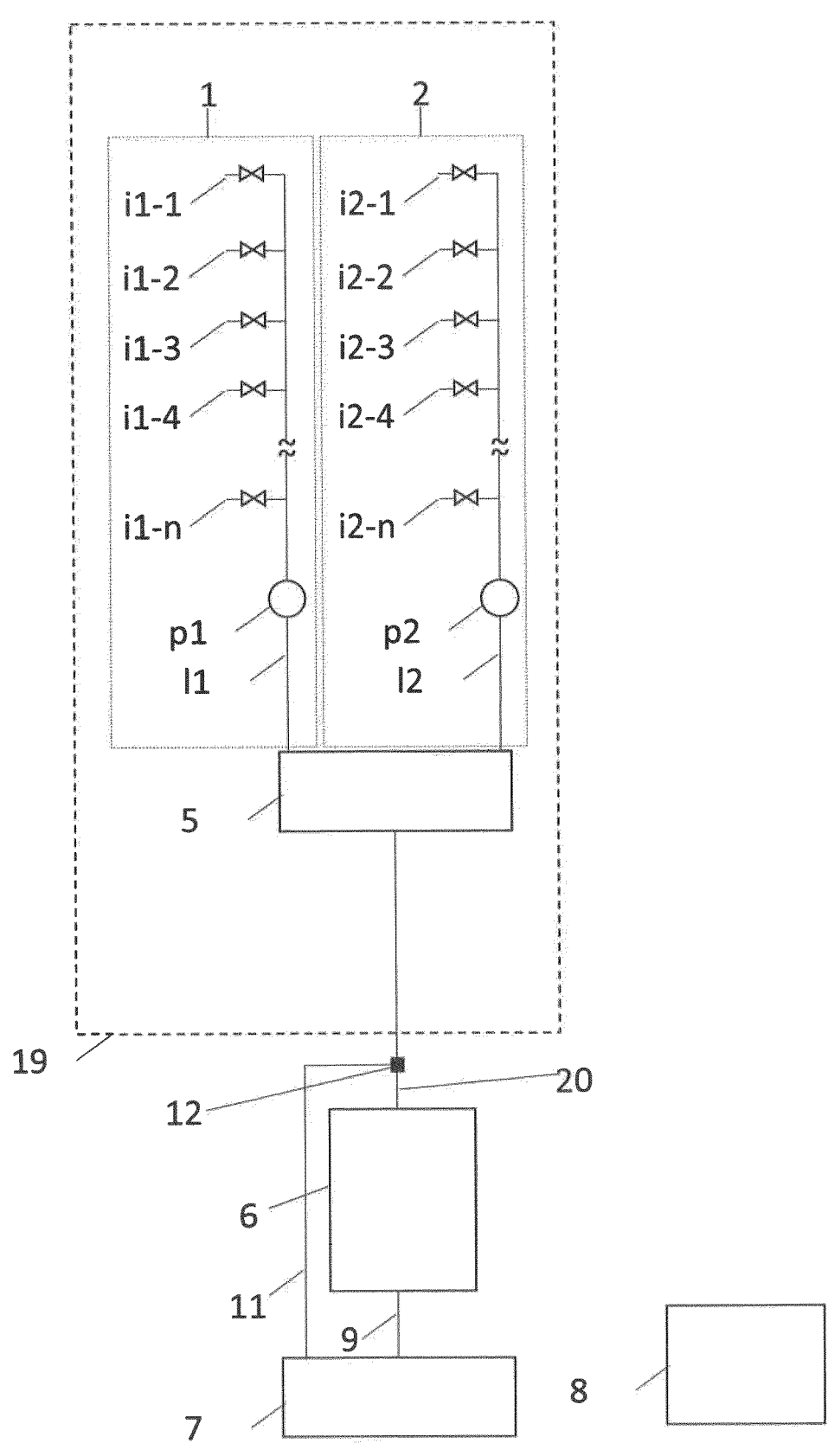

FIG. 7 shows a further embodiment of the apparatus in which the apparatus has two liquid supply lines. The apparatus of FIG. 7 essentially corresponds to the apparatus described with respect to FIG. 1, but comprises only two liquid supply lines 1, 2 and does not include sensors arranged downstream of the mixing device 5.

Figure 8:
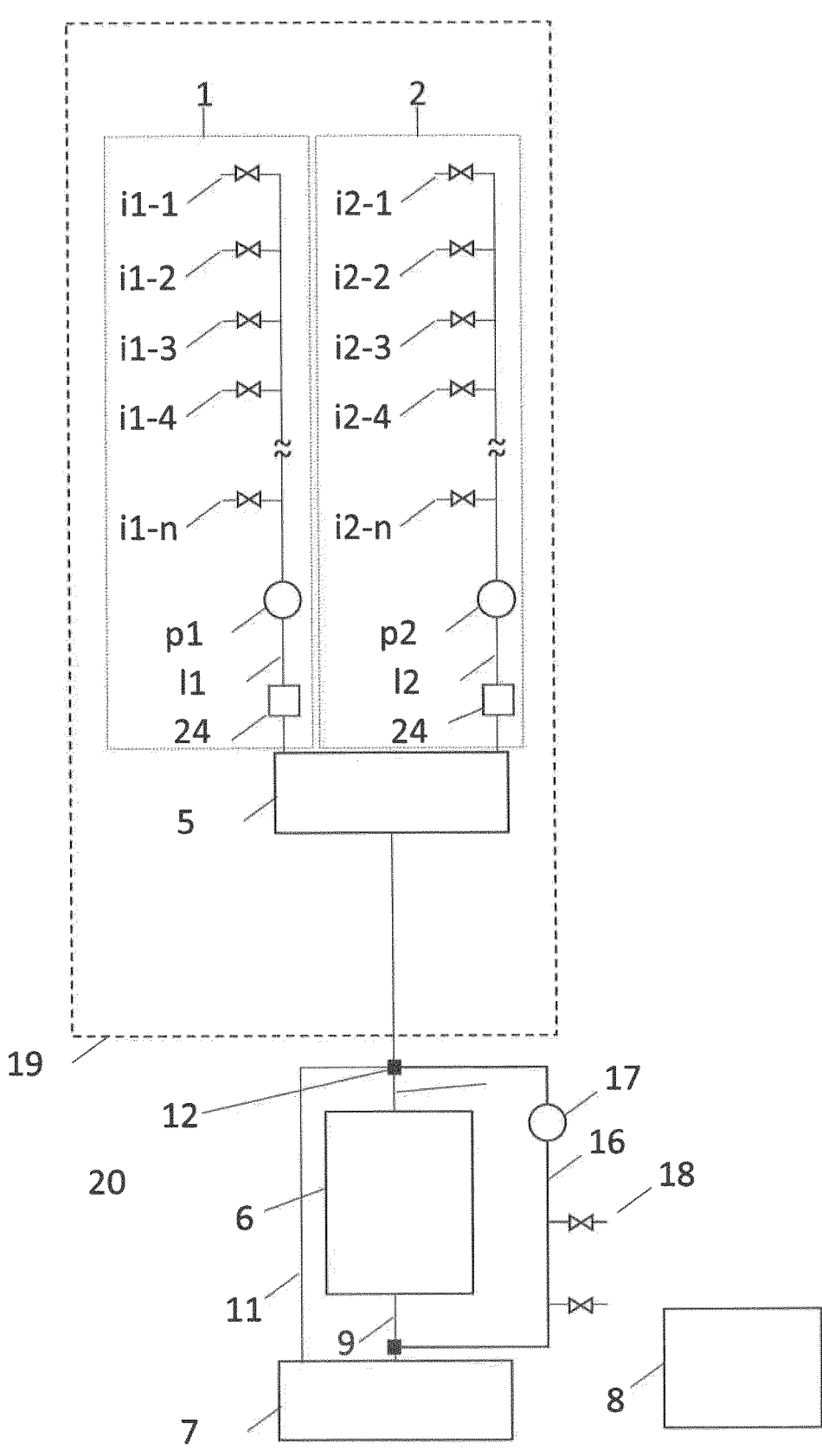

FIG. 8 shows another embodiment of the apparatus having two liquid supply lines and a recycling circuit. The apparatus of FIG. 8 essentially corresponds to the apparatus as described with respect to FIG. 7, but additionally includes the recycling circuit comprising the liquid recycling conduit 16 and the liquid pump 17. The recycling circuit as shown in FIG. 8 also comprises additional liquid inlets 18.

Further, the embodiment of FIG. 1 comprises liquid flow sensors 24 arranged in each of the two liquid supply lines 1, 2 which are arranged downstream of the respective liquid pump p1, p2 and upstream of the mixing device 5.

Figure 9:
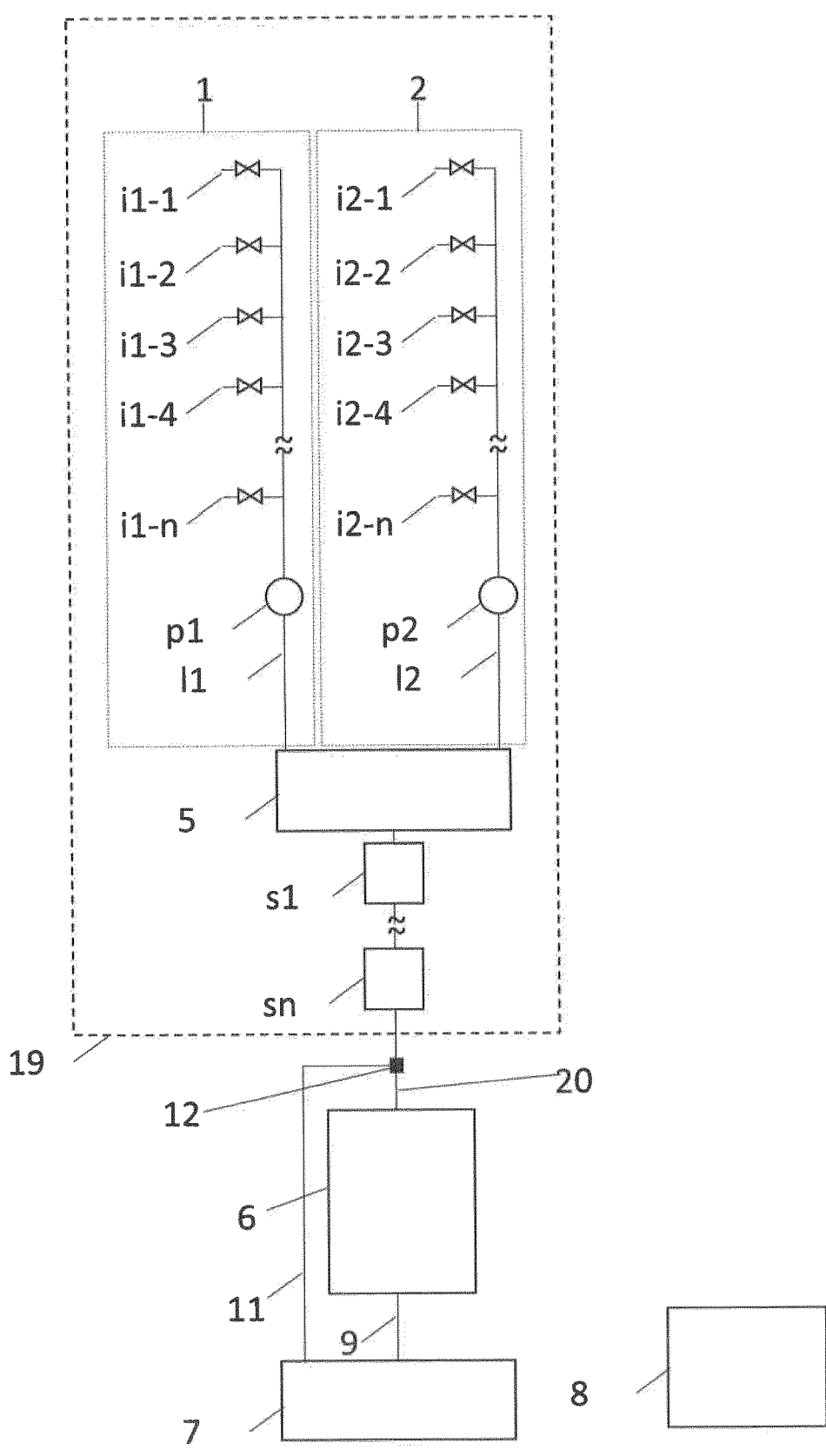

FIG. 9 shows an embodiment of the apparatus of FIG. 1 with only two liquid supply lines 1, 2. The explanations provided with respect to FIG. 1 also apply to the embodiment shown in FIG. 9, except for the omission of the two further liquid lines 3, 4.

Figure 10:
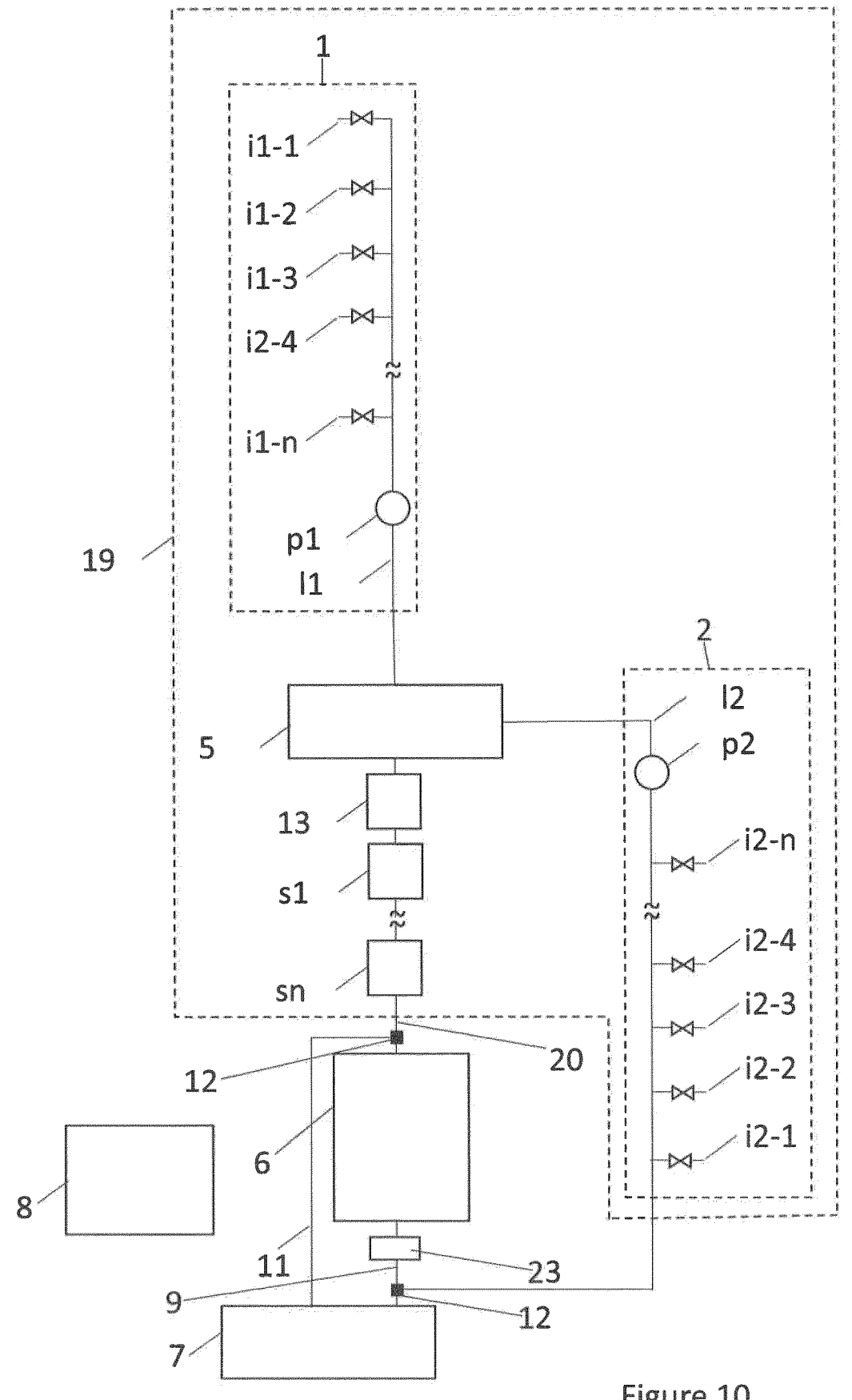

FIG. 10 shows an embodiment of the apparatus as described with respect to FIG. 3 but having only two liquid supply lines.

Figure 11:
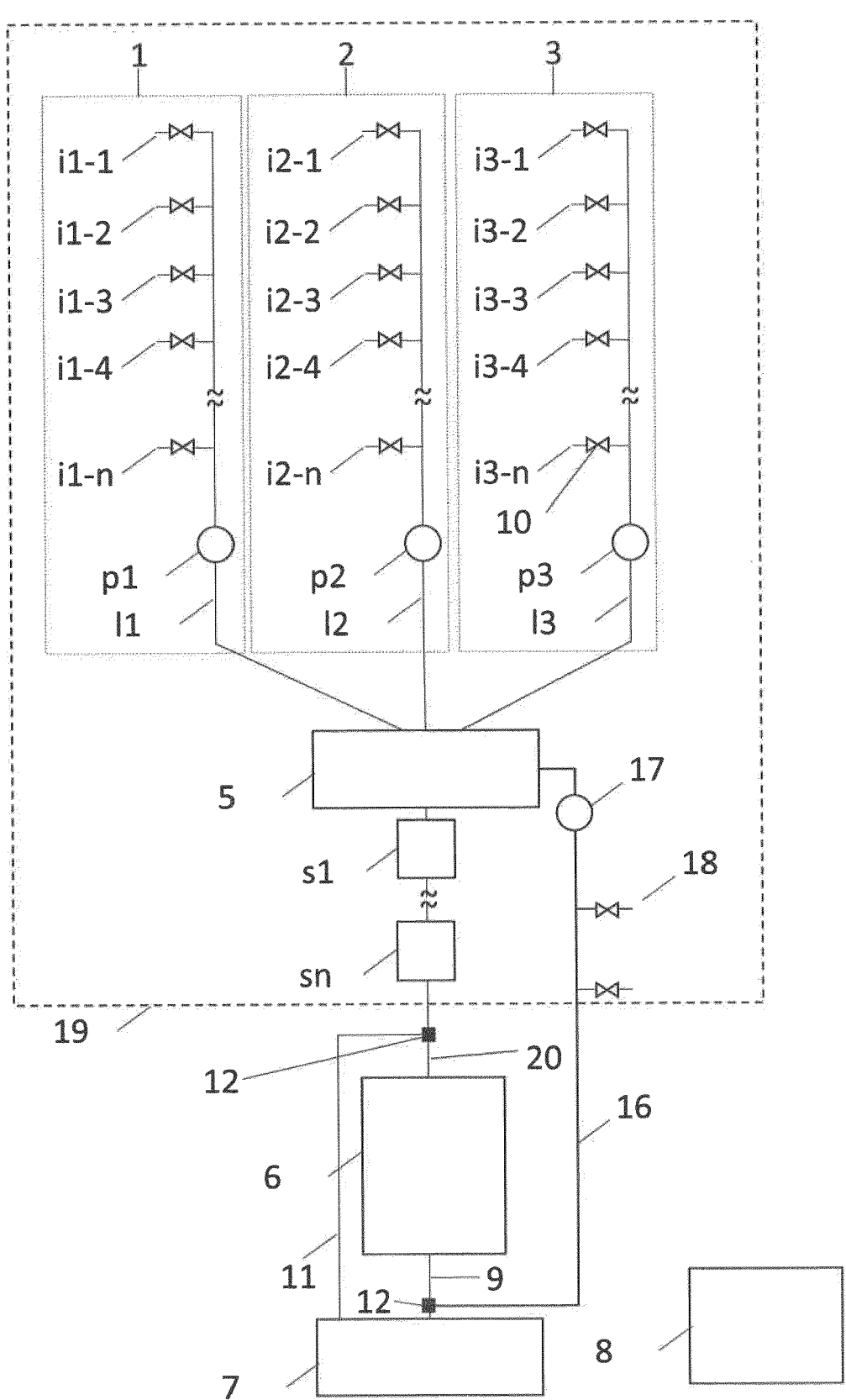

FIG. 11 shows an embodiment of the apparatus of FIG. 2 with only three liquid supply lines. Except for the reduction of the number of liquid supply lines 1, 2, the description of the embodiment of FIG. 2 also applies to the embodiment of FIG. 11.

Figure 12:
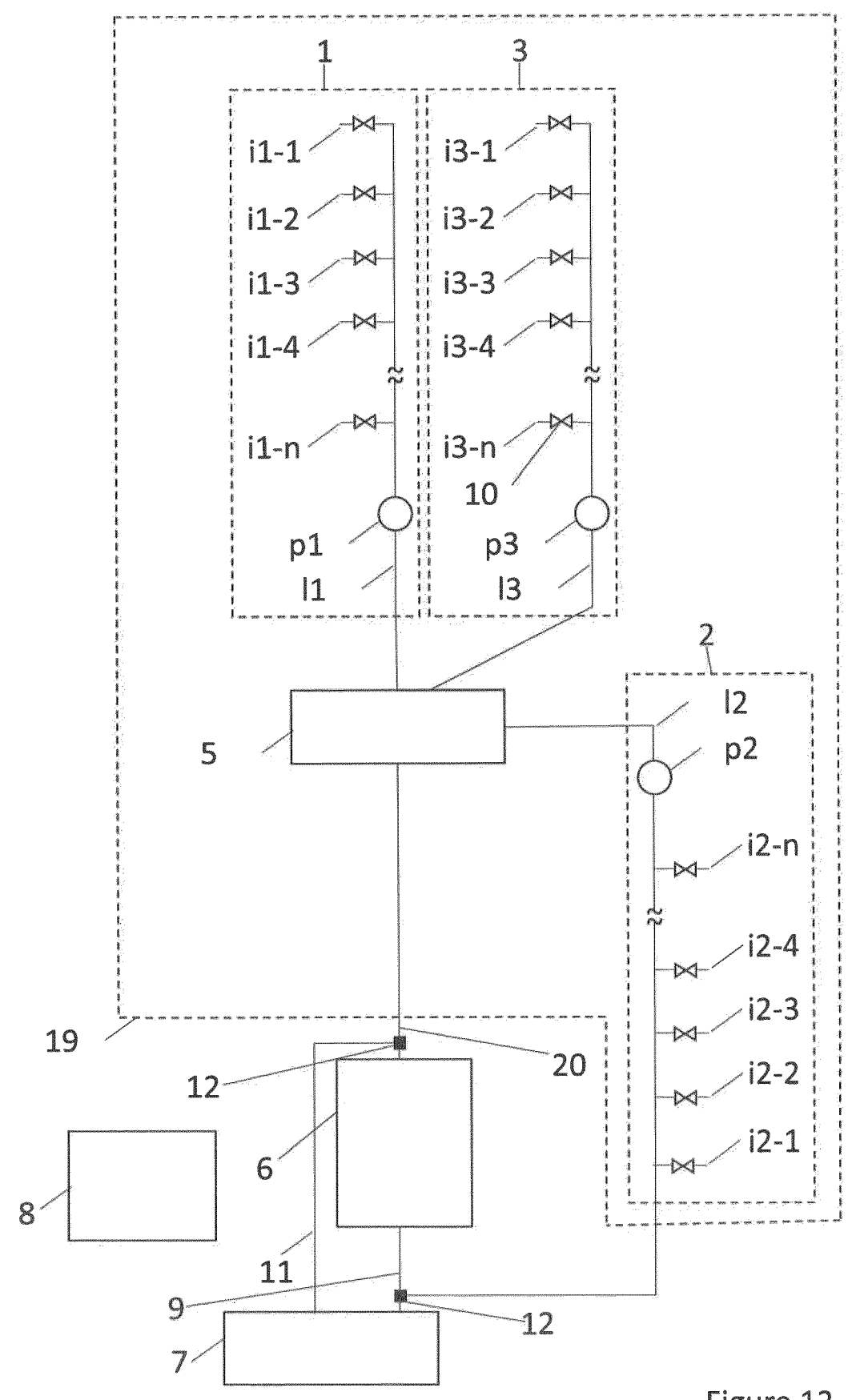

FIG. 12 shows another embodiment of the apparatus having three liquid supply lines, wherein one of the liquid supply lines serves as recycling circuit. The embodiment of FIG. 12 is similar to the embodiment described with respect to FIG. 3, except for the omission of the sensors and the fourth liquid supply line.

Figure 13:
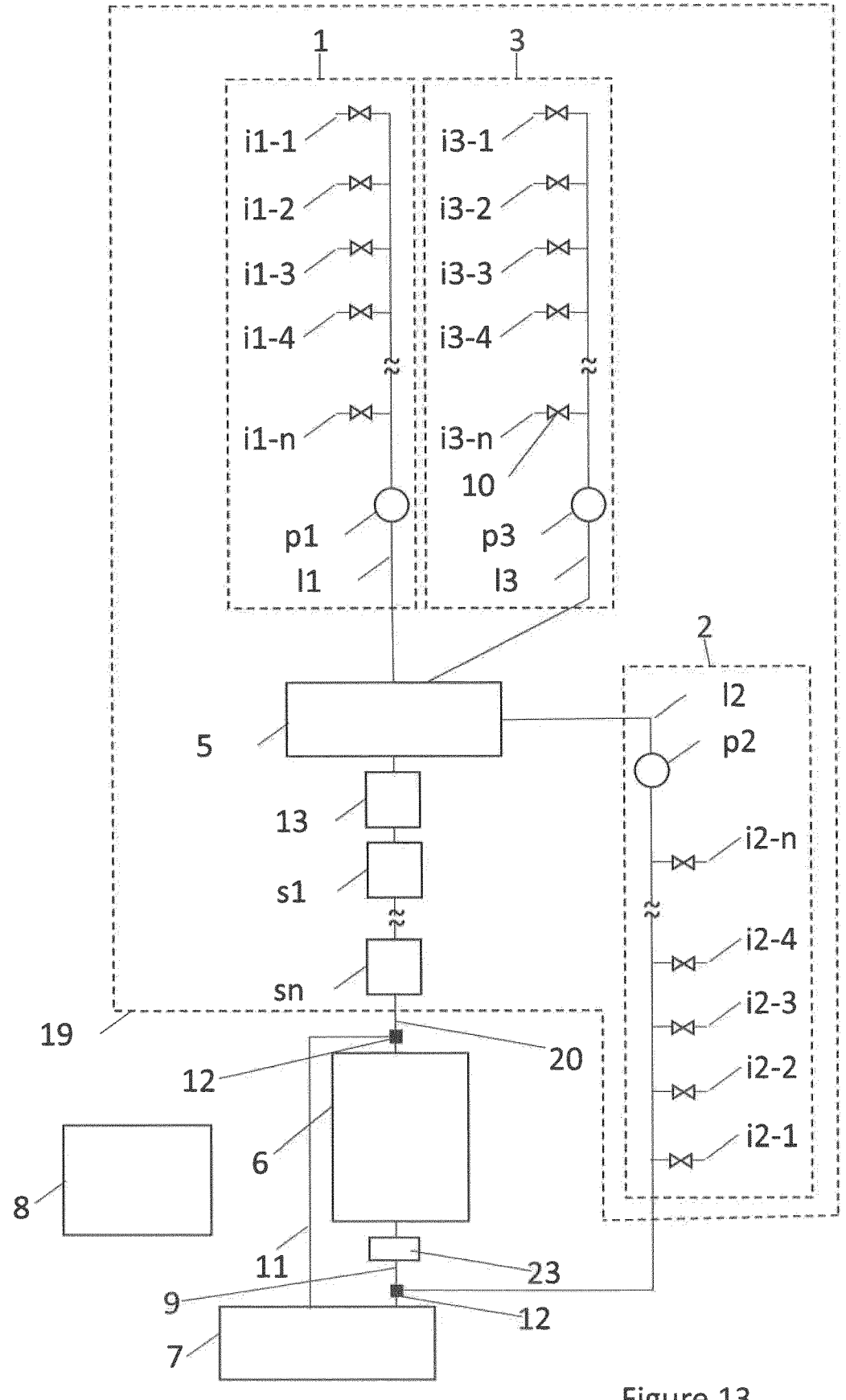

FIG. 13 shows a further embodiment of the apparatus of FIG. 3 with only three liquid supply lines. In contrast to the embodiment of FIG. 12, the sensors s1 . . . sn as well as sensor 23 are present.

The invention claimed is:

1. An apparatus for the automated synthesis of oligonucleotides, comprising:

a) a reaction vessel (6) connected via a liquid conduit (9) to a waste container (7);

b) a liquid supply unit (19) for delivering liquid reagents to the reaction vessel (6);

c) a bypass conduit (11), which allows to direct liquid flow from the liquid supply unit (19) into the waste container (7) without passage through the reaction vessel (6); and d) a control unit (8), wherein the liquid supply unit (19) comprises:

b-1) at least one mixing device (5), connected to b-2) at least two liquid supply lines (1, 2), each comprising at least one liquid conduit (l1, l2) with n liquid inlets (i1-$n$, i2-$n$), where n is an integer between 1 and 25, and at least one pump (p1, p2), wherein the control unit (8) is configured to individually define the composition of a deprotection reagent for each coupling cycle, and wherein the composition of the deprotection reagent is different between at least two coupling cycles.

2. The apparatus of claim 1, wherein at least the inner surfaces of the at least one mixing device (5) and of one of the at least two liquid supply lines (1, 2) are made from an acid-resistant material and/or comprise an acid resistant coating.

3. The apparatus of claim 2, wherein at least the inner surfaces of the at least one mixing device (5) and of one of the at least two liquid supply lines (1, 2) are made from an acid-resistant alloy and/or comprise an acid resistant polymeric coating.

4. The apparatus of claim 1, wherein the liquid supply unit (19) further comprises a third liquid supply line (3) connected to the at least one mixing device (5), the third liquid supply line (3) comprising at least one liquid conduit (13) with n liquid inlets (i3-*n*), where n is an integer between 1 and 25, and at least one liquid pump (p3).

5. The apparatus of claim 1, wherein the at least one mixing device (5) comprises a static mixer.

6. The apparatus of claim 1, further comprising n sensors (s1 to sn), where n is an integer equal to or larger than 1, which sensor(s) (s1 to sn) is/are positioned downstream of the at least one mixing device (5) and determine(s) at least one property of the liquid emerging from the mixing device (5).

7. The apparatus of claim 6, wherein at least one readout provided by at least one of the sensor(s) (s1 to sn) is used as a feedback signal to regulate the activity of one or more of the pumps comprised in the liquid supply unit (19).

8. The apparatus of claim 6, wherein at least one readout provided by at least one of the sensor(s) (s1 to sn) is used to control whether the liquid flow is directed into the reaction vessel (6) or into the waste container (7) without passage through the reaction vessel (6).

9. The apparatus of claim 1, further comprising at least one flow sensor (24) integrated into each of the at least two liquid supply lines (1, 2) upstream of the at least one mixing device (5), wherein at least one readout provided by the flow sensors is used as a feedback signal to regulate the activity of one or more of the at least one pump (p1, p2).

10. The apparatus of claim 1, wherein the liquid supply unit (19) further comprises at least one heat exchanger (13).

11. The apparatus of claim 6, comprising a conductivity sensor, a temperature sensor, and a UV absorption sensor.

12. The apparatus of claim 1, wherein the reaction vessel (6) is a packed column reactor or a batch reactor.

13. The apparatus of claim 1, further comprising a recycling circuit directing flow from the liquid conduit (9), which connects the reaction vessel to the waste container, back into the reaction vessel (6) by a pump (17).

14. The apparatus of claim 13, wherein the recycling circuit is comprised in one of the at least two liquid supply lines (1, 2), which is connected via one of its inlets (i1-*n*, i2-*n*) and a multi way valve (12) to the liquid conduit (9), and whose pump (p1, p2) may drive the recirculation of the fluid from the liquid conduit (9) via the at least one mixing device (5) back into the reaction vessel.

15. The apparatus of claim 1, wherein the control unit (8) is configured to control the execution of a synthesis protocol comprising at least two iterations of a coupling cycle, wherein the protocol individually defines the composition of an acidic deprotection reagent for each coupling cycle.

16. The apparatus of claim 1, wherein the control unit (8) directs the action of the at least one pump (p1, p2), so as to achieve a specific composition of the deprotection reagent in each of the coupling cycles.

17. A method of assembling an oligonucleotide chain in automated fashion by repeated cycles of building block coupling, wherein the following steps 1 through 6 are carried out anew in each of the cycles of building block coupling:

1. providing a n-mer oligonucleotide, where n is an integer equal to or larger than 1, bound to a solid support and comprising a first reactive group free to extend the oligonucleotide backbone by reaction with a second reactive group comprised in a building block to be incorporated;

2. providing the building block to be incorporated, which comprises the second reactive group free to react with the first reactive group of the n-mer oligonucleotide, and which further comprises a first reactive group blocked by an acid sensitive temporary protecting group;

3. contacting the n-mer oligonucleotide with the building block to be incorporated under conditions that allow for binding of the first reactive group of n-mer oligonucleotide to the second reactive group of the building block to be incorporated, and generating a protected, extended n-mer oligonucleotide, which is blocked from further extension by the acid sensitive temporary protecting group;

4. preparing an acidic deprotection reagent by mixing at least two liquid compositions, wherein the composition of the acidic deprotection reagent is defined individually for each coupling cycle, and wherein the composition of the acidic deprotection reagent is different between at least two coupling cycles;

5. contacting the protected, extended n-mer oligonucleotide of step 3 with the acidic deprotection reagent of step 4, thereby cleaving the acid sensitive temporary deprotecting group from the extended n-mer oligonucleotide; and 6. removing the deprotection reagent and soluble cleavage product from the extended n-mer oligonucleotide, which may then be used as the n-mer oligonucleotide in step 1 of the following coupling cycle.

18. The method of claim 17, wherein the content of acid in the deprotection reagent is selected from the range of 0.1% (w/w) to 50% (w/w) acid individually for each coupling cycle.

19. The method of claim 17, wherein the acid sensitive temporary protecting group is a trityl type protecting group.

20. The method of claim 17, wherein the first reactive group is a hydroxyl group.

21. The method of claim 20, wherein the second reactive group is selected from the group consisting of a phosphoamidite group and a H-phosphonate monoester group.

22. The method of claim 21, wherein step 3 comprises contacting the building block and the n-mer oligonucleotide under conditions, which allow for formation of a phosphite triester group, and mixing the resulting compound with an oxidizing reagent or a sulfurizing reagent to convert the phosphite triester group into a phosphate triester group or a thiophosphate triester group, respectively.

* * * * *